US012347541B1

(12) United States Patent
Demurjian et al.

(10) Patent No.: US 12,347,541 B1
(45) Date of Patent: Jul. 1, 2025

(54) CAREGIVER SYSTEM AND METHOD FOR INTERFACING WITH AND CONTROLLING A MEDICATION DISPENSING DEVICE

(71) Applicant: Aspargo Laboratories, Inc., New York, NY (US)

(72) Inventors: Adam Demurjian, Red Bank, NJ (US); Ravi Sawhney, Malibu, CA (US); Lance Hussey, Simi Valley, CA (US); Michael Kulick, Simi Valley, CA (US); Brian Weingarth, Woodland Hills, CA (US); Josh Probst, Culver City, CA (US); Rajvir Logani, Calabasas, CA (US); Cary Chow, Santa Monica, CA (US); Christianna Bethel, Glendale, CA (US); Craig Steel, El Segundo, CA (US); Michael Schuffert, Chatsworth, CA (US); John Vernon, Malibu, CA (US)

(73) Assignee: ASPARGO LABORATORIES, INC., New York, NY (US)

( * ) Notice: Subject to any disclaimer, the term of this patent is extended or adjusted under 35 U.S.C. 154(b) by 0 days.

(21) Appl. No.: 18/614,062

(22) Filed: Mar. 22, 2024

(51) Int. Cl.
*G16H 20/13* (2018.01)
*G16H 40/67* (2018.01)
*G16H 80/00* (2018.01)

(52) U.S. Cl.
CPC ............. *G16H 20/13* (2018.01); *G16H 40/67* (2018.01); *G16H 80/00* (2018.01)

(58) Field of Classification Search
CPC ........ G16H 20/13; G16H 40/67; G16H 80/00; G16H 20/10; G06Q 50/20–26; A61J 7/0481

See application file for complete search history.

(56) References Cited

U.S. PATENT DOCUMENTS

| 4,549,674 | A | 10/1985 | Alticosalian |
| 5,329,976 | A | 7/1994 | Haber |
| D349,958 | S | 8/1994 | Hollis |
| 5,542,760 | A | 8/1996 | Chanoch |

(Continued)

FOREIGN PATENT DOCUMENTS

| CA | 200492 | 6/1920 |
| CA | 222464 | 8/1922 |

(Continued)

OTHER PUBLICATIONS

Non-Final Office Action, U.S. Appl. No. 18/606,136, dated May 3, 2024.

(Continued)

*Primary Examiner* — Christopher L Gilligan
*Assistant Examiner* — Jessica Marie Webb
(74) *Attorney, Agent, or Firm* — RISSO I.P.

(57) ABSTRACT

The present disclosure provides a caregiver system and method for interfacing with and controlling an oral medication dispensing device. The system registers the caregiver and provides the caregiver a list of patients under the caregiver's care, as well as associated medication dose schedules for each of the one or more patients. The caregiver is provided reminders regarding doses and allowed to modify the dose schedule to generate a modified dose schedule. The modified does schedule is pushed to a patient system associated with a medication dispensing device.

17 Claims, 36 Drawing Sheets

(56) References Cited

U.S. PATENT DOCUMENTS

| | | |
|---|---|---|
| 6,907,876 B1 | 6/2005 | Clark |
| D509,296 S | 9/2005 | Minshull et al. |
| D650,696 S | 12/2011 | Peden, III |
| D654,806 S | 2/2012 | Lorenz |
| 8,141,550 B2 | 3/2012 | Lawrence |
| D669,791 S | 10/2012 | Peden, III |
| D673,862 S | 1/2013 | Garcia |
| D693,457 S | 11/2013 | Mayer |
| D696,772 S | 12/2013 | Schneider et al. |
| D696,964 S | 1/2014 | Chen |
| D751,415 S | 3/2016 | Otani |
| 9,277,797 B2 | 3/2016 | Chen |
| 9,501,618 B1* | 11/2016 | Wurst .................. G06F 21/6254 |
| D776,264 S | 1/2017 | Tyce |
| D778,492 S | 2/2017 | Liu |
| D801,507 S | 10/2017 | Kelnhofer |
| 9,980,140 B1 | 5/2018 | Spencer |
| D825,098 S | 8/2018 | Fornarelli |
| D827,128 S | 8/2018 | Boyaval et al. |
| 10,127,360 B2 | 11/2018 | Chack |
| 10,204,704 B1 | 2/2019 | Wurst |
| D869,647 S | 12/2019 | Dorsey |
| D892,628 S | 8/2020 | Caruso |
| 10,765,817 B2 | 9/2020 | Boyden |
| D898,900 S | 10/2020 | Atterbury et al. |
| D912,805 S | 3/2021 | Lee-sepsick et al. |
| D914,514 S | 3/2021 | Wintroub |
| D918,381 S | 5/2021 | Luong |
| D921,981 S | 6/2021 | Sudlow |
| D926,968 S | 8/2021 | Kern et al. |
| 11,154,461 B1 | 10/2021 | Abbs |
| D936,569 S | 11/2021 | Liu |
| D956,211 S | 6/2022 | Bourelle et al. |
| D958,329 S | 7/2022 | Bourelle et al. |
| D959,651 S | 8/2022 | Farmer |
| D962,423 S | 8/2022 | Melander et al. |
| D968,594 S | 11/2022 | Toldi |
| D969,315 S | 11/2022 | Yamamoto |
| D973,866 S | 12/2022 | Bourelle et al. |
| 11,517,673 B2 | 12/2022 | Pedersen |
| 11,524,115 B2 | 12/2022 | Jacobsen |
| 11,534,111 B2 | 12/2022 | Chae |
| D974,547 S | 1/2023 | O'Malley et al. |
| 11,576,842 B2 | 2/2023 | Park |
| D980,083 S | 3/2023 | Siegel |
| 11,598,664 B2 | 3/2023 | McDermott |
| 11,605,451 B2 | 3/2023 | Barbosa De Abreu E Sousa |
| 11,607,496 B2 | 3/2023 | Fabricius |
| D984,640 S | 4/2023 | Suzuki |
| 11,623,049 B2 | 4/2023 | Pedersen |
| D985,116 S | 5/2023 | Davis et al. |
| D985,117 S | 5/2023 | Davis et al. |
| D985,118 S | 5/2023 | Davis et al. |
| D985,119 S | 5/2023 | Melander et al. |
| 11,676,693 B2 | 6/2023 | Mercolino |
| 11,707,093 B2 | 7/2023 | Moloney |
| 11,717,667 B2 | 8/2023 | Bochenko |
| 11,738,147 B2 | 8/2023 | Olesen |
| D998,138 S | 9/2023 | Espinoza |
| D998,233 S | 9/2023 | Song |
| D1,001,272 S | 10/2023 | Boyaval et al. |
| D1,002,838 S | 10/2023 | Dennisur et al. |
| 11,771,591 B2 | 10/2023 | Agarwal |
| D1,010,817 S | 1/2024 | Diluzio et al. |
| 11,865,299 B2 | 1/2024 | Estes |
| 11,872,375 B2 | 1/2024 | Plaschkes |
| 11,901,059 B2* | 2/2024 | Pugsley ................ A61J 7/0084 |
| 11,929,160 B2 | 3/2024 | Edwards |
| 11,931,552 B2 | 3/2024 | Bar-El |
| D1,025,471 S | 4/2024 | Tao |
| 11,980,739 B2 | 5/2024 | Pizzochero |
| 11,998,057 B2 | 6/2024 | Moloney |
| 12,005,241 B2 | 6/2024 | Pedersen |
| 12,042,614 B2 | 7/2024 | Johnston |
| D1,038,381 S | 8/2024 | Demurjian |
| 12,053,615 B2 | 8/2024 | Estes |
| 12,064,591 B2 | 8/2024 | Estes |
| 12,106,836 B1 | 10/2024 | Demurjian |
| 2002/0169635 A1 | 11/2002 | Shillingburg |
| 2003/0216831 A1* | 11/2003 | Hart ...................... G16H 15/00 |
| | | 700/235 |
| 2005/0073832 A1 | 4/2005 | Shilton |
| 2006/0027233 A1 | 2/2006 | Zierenberg |
| 2006/0071027 A1 | 4/2006 | Davies |
| 2009/0294521 A1 | 12/2009 | De La Huerga |
| 2009/0302062 A1 | 12/2009 | Maddy |
| 2010/0096408 A1 | 4/2010 | Schiewe |
| 2010/0211005 A1* | 8/2010 | Edwards ................ A61P 19/02 |
| | | 604/82 |
| 2011/0000170 A1* | 1/2011 | Burg ...................... G16H 20/10 |
| | | 53/238 |
| 2011/0168175 A1 | 7/2011 | Dunne |
| 2012/0035546 A1 | 2/2012 | Cabiri |
| 2013/0090594 A1 | 8/2013 | Day |
| 2013/0211327 A1 | 8/2013 | Osman |
| 2013/0221097 A1 | 9/2013 | Kouyoumjian |
| 2013/0245604 A1 | 9/2013 | Kouyoumjian et al. |
| 2013/0253433 A1 | 9/2013 | Senior |
| 2014/0000588 A1 | 1/2014 | Le Maner |
| 2014/0081234 A1 | 3/2014 | Eggert |
| 2014/0323883 A1 | 10/2014 | Fahey |
| 2014/0323963 A1 | 10/2014 | West |
| 2014/0326238 A1 | 11/2014 | Spandorfer |
| 2015/0257979 A1 | 9/2015 | Jenema |
| 2015/0288797 A1* | 10/2015 | Vincent ................. G16H 10/60 |
| | | 455/404.2 |
| 2015/0364057 A1* | 12/2015 | Catani ................... G16H 10/60 |
| | | 434/262 |
| 2016/0050975 A1 | 2/2016 | Worm |
| 2017/0007763 A1 | 1/2017 | McLoughlin et al. |
| 2017/0053098 A1 | 2/2017 | Hawkins |
| 2017/0091392 A1 | 3/2017 | White |
| 2017/0277937 A1 | 9/2017 | Baek |
| 2017/0283151 A1* | 10/2017 | Stormer ................ G16H 20/10 |
| 2017/0326033 A1 | 11/2017 | Kraft |
| 2018/0071425 A1* | 3/2018 | Jin ......................... A61L 9/125 |
| 2018/0342329 A1* | 11/2018 | Rufo ..................... G16H 40/67 |
| 2018/0369070 A1 | 12/2018 | Gielen |
| 2019/0001085 A1 | 1/2019 | Cottenden |
| 2019/0240430 A1 | 8/2019 | Jackson |
| 2020/0022416 A1 | 1/2020 | Alarcon |
| 2020/0022418 A1 | 1/2020 | Belisle |
| 2020/0187565 A1 | 6/2020 | Williams et al. |
| 2020/0360239 A1 | 11/2020 | Campos |
| 2020/0384188 A1 | 12/2020 | Becker |
| 2020/0384216 A1 | 12/2020 | Eicher |
| 2021/0030626 A1 | 2/2021 | Medhal |
| 2021/0104304 A1 | 4/2021 | Davidovics |
| 2021/0146066 A1 | 5/2021 | Wuttke |
| 2021/0154417 A1 | 5/2021 | Cheng |
| 2021/0225503 A1* | 7/2021 | Dejonge ................ A61J 7/0481 |
| 2021/0236752 A1 | 8/2021 | Botha |
| 2021/0257068 A1* | 8/2021 | Clarke ..................... H04W 4/80 |
| 2021/0264716 A1 | 8/2021 | Norbeck |
| 2021/0268217 A1 | 9/2021 | Botha |
| 2021/0290491 A1 | 9/2021 | Campos |
| 2021/0319782 A1 | 10/2021 | Gong |
| 2021/0338948 A1 | 11/2021 | Mellinger |
| 2021/0361879 A1 | 11/2021 | Gjertsen |
| 2021/0378916 A1 | 12/2021 | Shalon |
| 2022/0071849 A1 | 3/2022 | Hayman |
| 2022/0131699 A1* | 4/2022 | Kimmel .............. H04L 63/0861 |
| 2022/0269763 A1 | 8/2022 | Lett |
| 2022/0287915 A1* | 9/2022 | LeBrun ................. G16H 20/10 |
| 2022/0379046 A1 | 12/2022 | Decock |
| 2023/0036333 A1 | 2/2023 | Park |
| 2023/0065458 A1* | 3/2023 | Abadi .................... G16H 40/67 |
| 2023/0248614 A1 | 8/2023 | Aon |
| 2023/0321372 A1 | 10/2023 | Fabien |
| 2024/0090588 A1 | 3/2024 | Barbaric |

(56) References Cited

U.S. PATENT DOCUMENTS

FOREIGN PATENT DOCUMENTS

| WO | 2012013723 A1 | 2/2012 | | |
|---|---|---|---|---|
| WO | 2012109222 A2 | 8/2012 | | |
| WO | WO-2022165349 A1 | * | 8/2022 | ................ A61J 1/03 |

OTHER PUBLICATIONS

"Medication Dispense and Monitoring System using Biometric Fingerprint-Recognition Authentication," An IP.com Prior Art Database Technical Disclosure; Authors et. al.: IBM; Original Publication Date: Aug. 29, 2003; IP.com No. PCOM000019130D; IP.com Electronic Publication Date: Aug. 29, 2003 (Year: 2003).
Flonq Max Smart Disposable Vape, Fiona, [Postdate unknown], [Site seen: May 13, 2024], Seen at URL: https://www.flonq.global/blog-news/flonq-max-smart-disposable-vape-top-notch-tech-meets-impressive-performance-in-2024 (Year: 2024).
Lauren Golik, "Can We Pump the Brakes on Pumps?", Beauty Independent, Jul. 25, 2020.
Mole, Beth, "E-cig co. put Viagra, Cialis in vape liquids—the FDA is throbbing mad," Ars Technica, [Post date: Oct. 12, 2018], [Site seen: May 13, 2024], Seen at URL: https://arstechnica.com/science/2018/10/ fda-issues-stiff-warning-to-e-cig-seller-who-put-viagra-in-vape-liquid/ (Year: 2018).
Notice of Allowance dated Jun. 21, 2024 for U.S. Appl. No. 18/606,136 (pp. 1-3).
Notice of Allowance dated Jun. 27, 2024 for U.S. Appl. No. 18/606,136 (pp. 1-2).
Notice of Allowance dated Jul. 8, 2024 for U.S. Appl. No. 18/606,136 (pp. 1-2).
Office Action dated May 3, 2024 for U.S. Appl. No. 18/606,136 (pp. 1-8).
Office Action dated Jun. 27, 2024 for U.S. Appl. No. 18/655,722 (pp. 1-10).
Office Action dated Jul. 3, 2024 for U.S. Appl. No. 18/601,329 (pp. 1-11).
Office Action dated Jul. 31, 2024 for U.S. Appl. No. 18/600,402 (pp. 1-9).
Office Action dated Jun. 3, 2024 for U.S. Appl. No. 18/614,041 (pp. 1-22).
Office Action dated May 22, 2024 for U.S. Appl. No. 18/614,085 (pp. 1-9).
Office Action dated May 30, 2024 for U.S. Appl. No. 18/606,151 (pp. 1-10).
Patil et al., "An IoT based Smart Medicine Dispenser Model for Healthcare," 2022 IEEE World Conference on Applied Intelligence and Computing; DOI: 10.1109/AIC55036.2022.9848934. (Year: 2022).
Perez et al., Evaluation of a Tracking System for Patients and Mixed Intravenous Medication Based on RFID Technology, Nov. 30, 2016, Sensors, pp. 1-15. (Year: 2016).
Shanthini et al., "Design and Implementation of IoT based Automatic Medicine Dispenser for Patients," Proceedings of the Third International Conference on Innovative Mechanisms for Industry Applications (ICIMIA 2023); DOI: 10.1109/ICIMIA60377.2023. 10426176. (Year: 2023).
Sildenafil Spray, Aspargo Labs, [post date unknown], [site seen May 13, 2024], Seen at URL: https://aspargolabs.com/ (Year: 2024).
Notice of Allowance dated Aug. 14, 2024 for U.S. Appl. No. 18/606,136 (pp. 1-2).
Office Action (Non-Final Rejection) dated Oct. 23, 2024 for U.S. Appl. No. 18/606,173 (pp. 1-11).
Office Action dated Aug. 29, 2024 for U.S. Appl. No. 18/614,085 (pp. 1-12).
Office Action dated Sep. 11, 2024 for U.S. Appl. No. 18/614,041 (pp. 1-27).
Office Action dated Sep. 13, 2024 for U.S. Appl. No. 18/600,198 (pp. 1-12).
Office Action dated Nov. 13, 2024 for U.S. Appl. No. 18/601,329 (pp. 1-17).
Office Action dated Nov. 13, 2024 for U.S. Appl. No. 18/655,722 (pp. 1-8).
Office Action dated Nov. 18, 2024 for U.S. Appl. No. 18/600,402 (pp. 1-8).
International Search Report and Written Opinion issued in App. No. PCT/US2024/047468, dated Dec. 11, 2024, 8 pages.
International Search Report and Written Opinion issued in App. No. PCT/US2024/047482, dated Dec. 12, 2024, 9 pages.
International Search Report and Written Opinion issued in App. No. PCT/US2024/047497, dated Dec. 11, 2024, 8 pages.
International Search Report and Written Opinion issued in App. No. PCT/US2024/047676, dated Jan. 27, 2025, 7 pages.
International Search Report and Written Opinion issued in App. No. PCT/US2024/047686, dated Dec. 11, 2024, 8 pages.
International Search Report and Written Opinion issued in App. No. PCT/US2024/047694, dated Dec. 11, 2024, 8 pages.
Notice of Allowance dated Jan. 16, 2025 for U.S. Appl. No. 18/600,198 (pp. 1-13).
Notice of Allowance dated Mar. 12, 2025 for U.S. Appl. No. 18/601,329 (pp. 1-11).
Notice of Allowance dated Mar. 31, 2025 for U.S. Appl. No. 18/655,722 (pp. 1-9).
Office Action dated Jan. 30, 2025 for U.S. Appl. No. 18/606,151 (pp. 1-12).
Office Action dated Feb. 6, 2025 for U.S. Appl. No. 18/606,173 (pp. 1-12).
Office Action dated Mar. 3, 2025 for U.S. Appl. No. 18/600,402 (pp. 1-13).
Office Action dated Mar. 14, 2025 for U.S. Appl. No. 18/614,085 (pp. 1-9).
Office Action dated Apr. 23, 2025 for U.S. Appl. No. 18/999,334 (pp. 1-12).
Offie Action dated Feb. 20, 2025 for U.S. Appl. No. 18/614,041 (pp. 1-17).

* cited by examiner

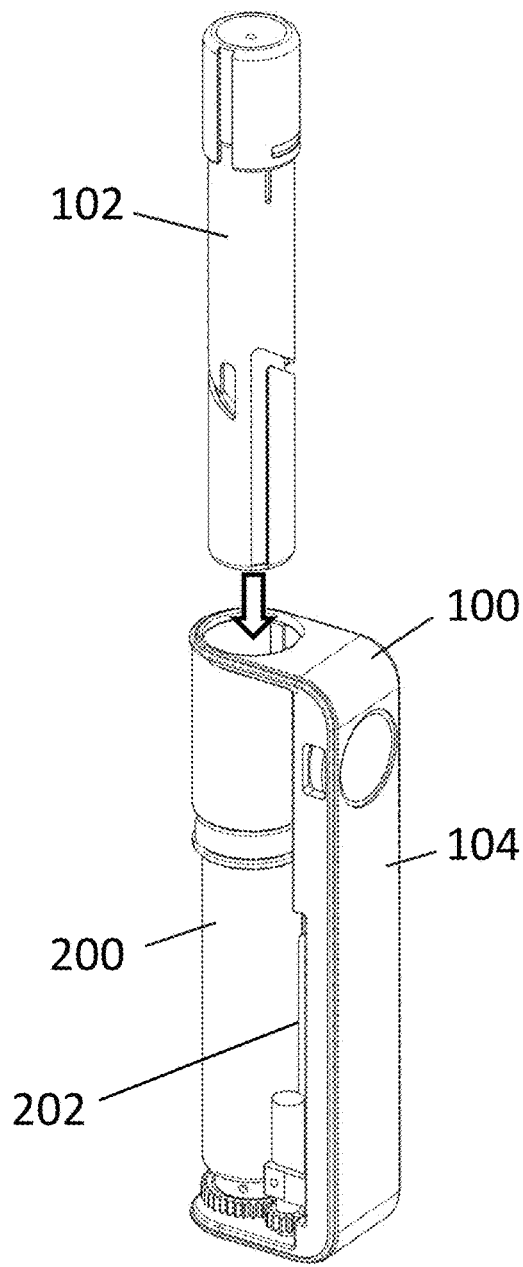
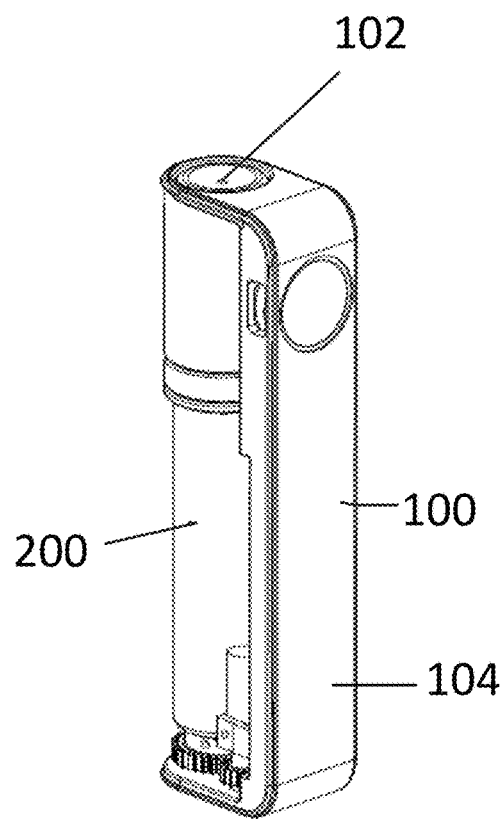
FIG. 2A
FIG. 2B

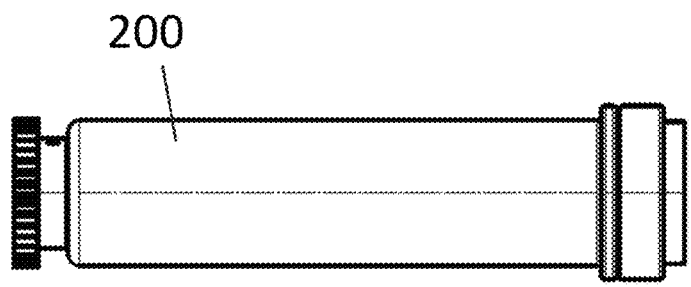
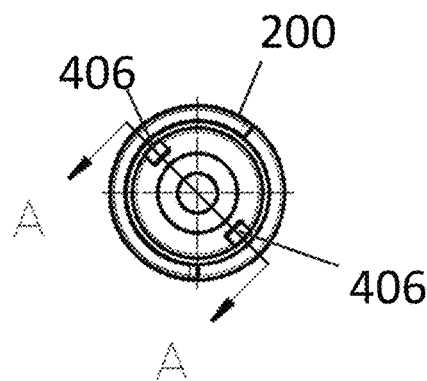
FIG. 5A   FIG. 5B
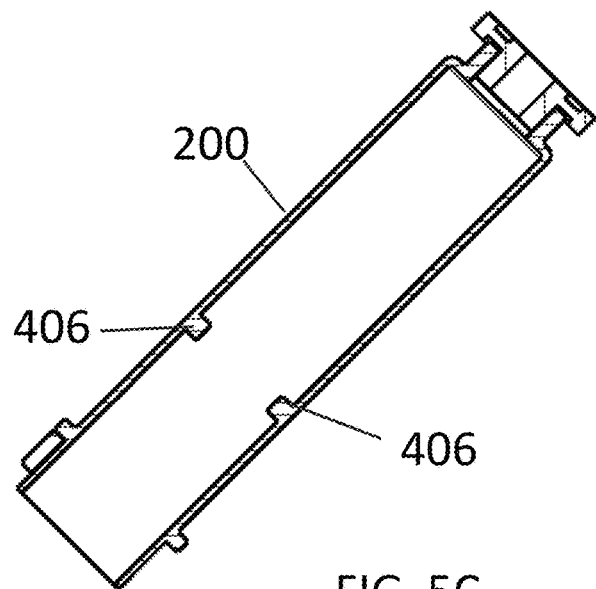
FIG. 5C

102

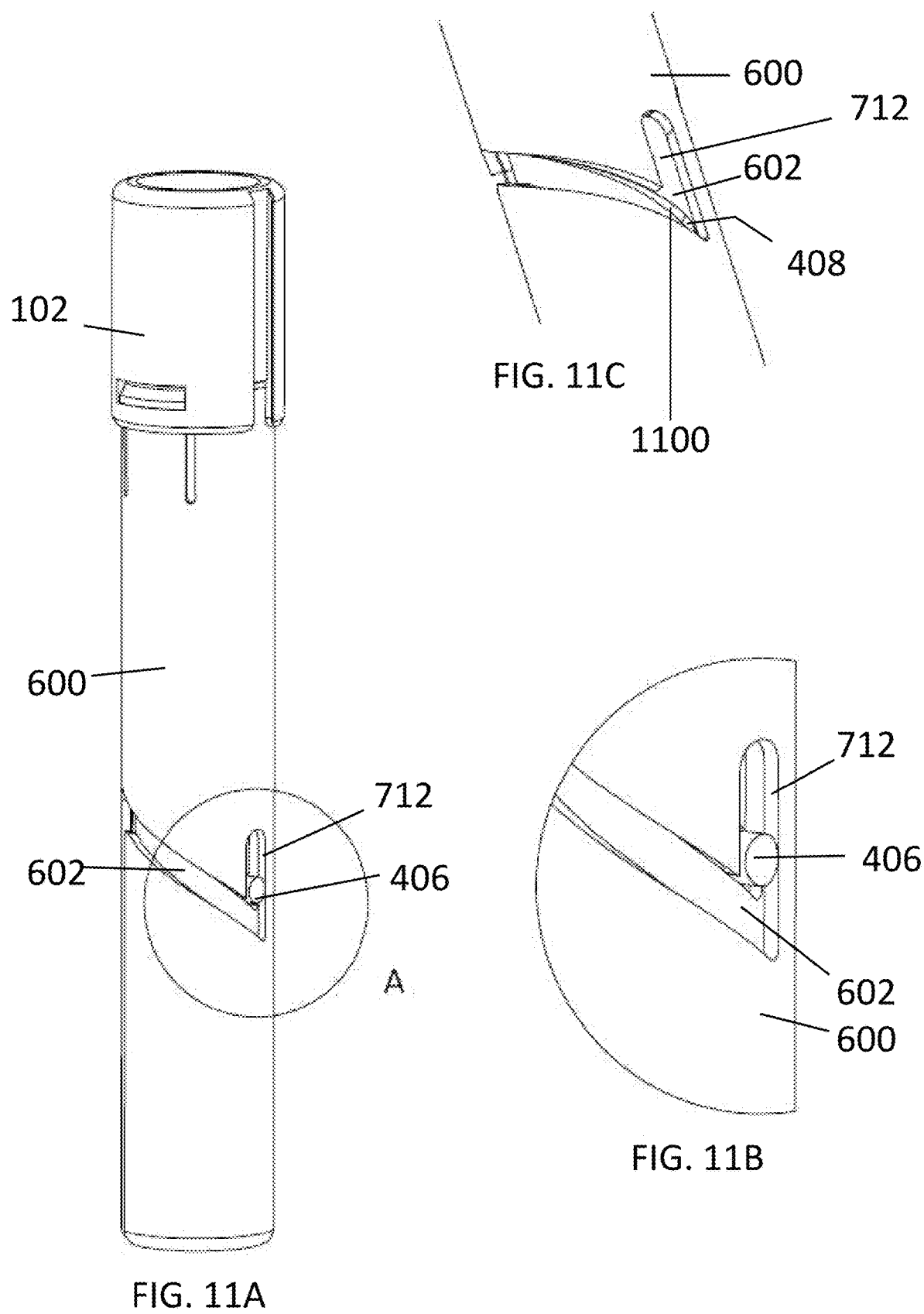

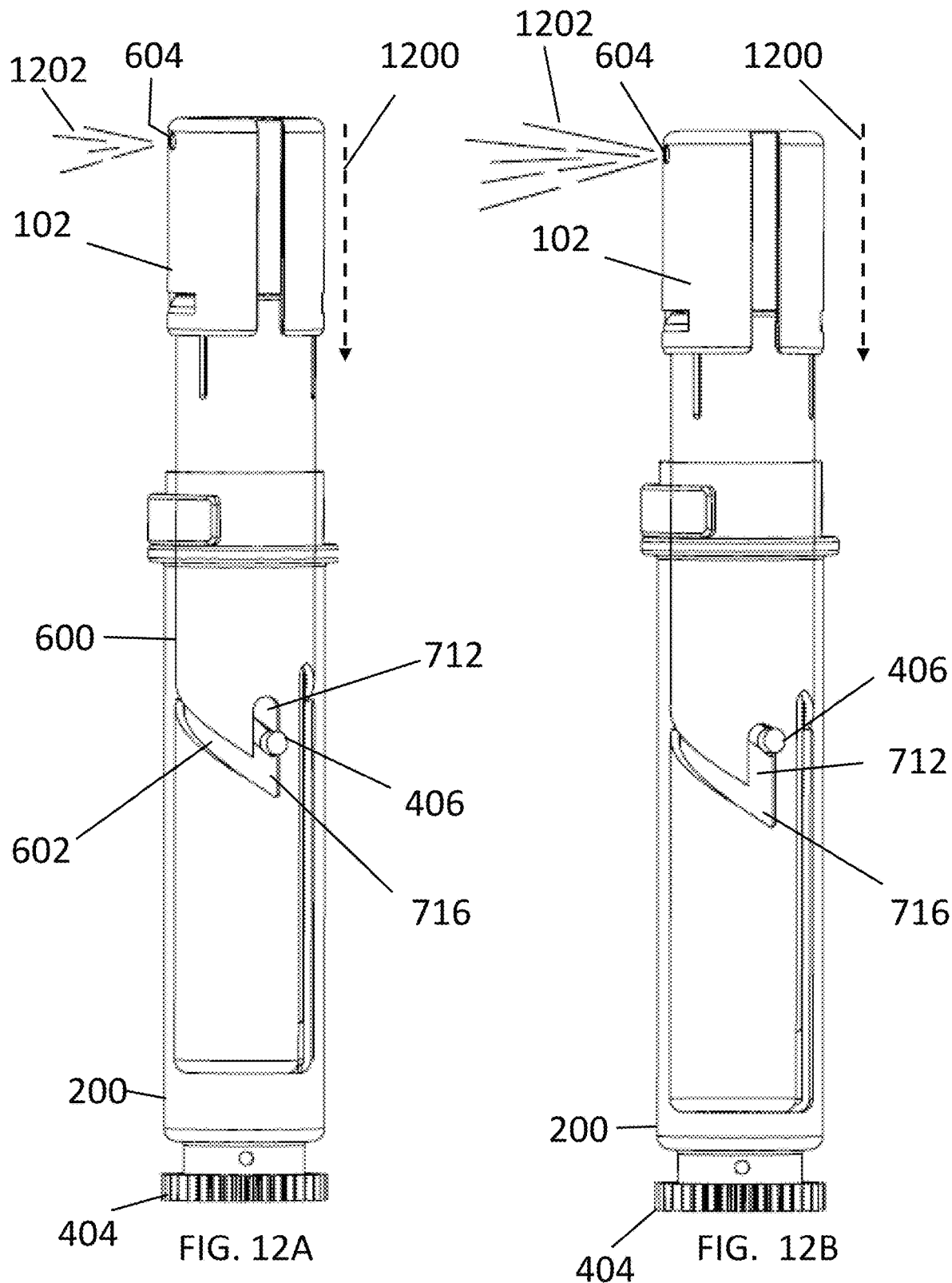

CAREGIVER SYSTEM AND METHOD FOR INTERFACING WITH AND CONTROLLING A MEDICATION DISPENSING DEVICE

BACKGROUND OF THE INVENTION

(1) Field of Invention

The present invention relates to a medication dispensing system and, more particularly, to a caregiver system and method for interfacing with and controlling a medication dispensing device.

(2) Description of Related Art

The field of medication treatment has grown increasingly complex in recent years, with patients frequently needing to manage and administer multiple types of medication. Under such circumstances, it is vital to provide reliable, accessible, and simple methodologies to patients for dispensing their medications. Many existing dispensing devices, however, tend to be cumbersome, confusing, or inefficient. Often, they rely on patients having to manually change their medication reminders or products, which can involve complicated steps or create potential for mistakes, like grabbing the wrong medication or dispensing an incorrect dosage. Furthermore, mistakes may potentially have serious health implications. Hence, it's vital to design an easy-to-use and fail-safe medication dispensing device that can be interacted with and/or controlled by a patient, caregiver, or doctor based on the personal prescription or medication regimen as applicable to a particular user.

One embodiment disclosed herein pertains to both a patient and caregiver system that can be used to interface with and/or control a medication dispensing device. The purpose of this design is not only to make medication administration simpler and more efficient but also to mitigate potential errors between users through wireless control by an associated system (patient or caregiver) having a software application stored on a wireless device (e.g., mobile phone, etc.). Both the patient and caregiver systems can be used to control a variety of features, such as user authentication and operation of the dispensing device, further enhancing safety measures. The innovative design allows the systems to interface with and/or control the medication dispensing device can significantly aid patients to manage and administer their medication effectively and safely.

SUMMARY OF INVENTION

The present disclosure provides a caregiver system and method for interfacing with and controlling a medication dispensing device. The purpose of this design is not only to make medication administration simpler and more efficient but also to mitigate potential errors associated with different users. The system includes one or more processors and associated memory. The memory is a non-transitory computer-readable medium having executable instructions encoded thereon, such that upon execution of the instructions, the one or more processors perform operations of registering a caregiver; providing the caregiver a list of one or more patients under the caregiver's care and associated medication dose schedules for each of the one or more patients; modifying the dose schedule for at least one of the one or more patients to generate a modified dose schedule; and pushing the modified dose schedule to a patient system associated with a medication dispensing device.

In another aspect, in pushing the modified dose schedule to a patient system associated with a medication dispensing device, the medication device is activated to dispense a medication dose if the medication dose is within the modified dose schedule.

In yet another aspect, the system performs an operation of modifying authentication information regarding at least one of the one or more patients, such as editing a fingerprint record.

In another aspect, the system performs an operation of recording notes regarding at least one of the one or more patients for viewing by a user of an associated doctor portal system.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 2A shows an interior-view of the medication dispensing device, depicting a cartridge carrier;

FIG. 2B shows an interior-view of the medication dispensing device, depicting the medication cartridge inserted into the cartridge carrier;

FIG. 5A shows a side-view illustration of the medication cartridge;

FIG. 5B shows a top-view illustration of the medication cartridge;

FIG. 5C is a cross-sectional, side-view illustration of the medication cartridge, taken from line A-A of FIG. 5B;

FIG. 11A shows an exemplary illustration of the medication cartridge, depicting the vial sliding within the shell;

FIG. 11B shows close-up view of Detail A, taken from FIG. 11A;

FIG. 11C shows an exemplary illustration of the medication cartridge, depicting the vial within the shell;

FIG. 12A shows an exemplary illustration of the medication cartridge within the cartridge carrier, depicting the medication cartridge in the dispensing position and being pressed downward to activate the pump assembly and dispense medication from the medication cartridge;

FIG. 12B shows an exemplary illustration of the medication cartridge within the cartridge carrier, depicting the medication cartridge in the dispensing position and being pressed downward to activate the pump assembly and dispense medication from the medication cartridge;

DETAILED DESCRIPTION

Figure 1:
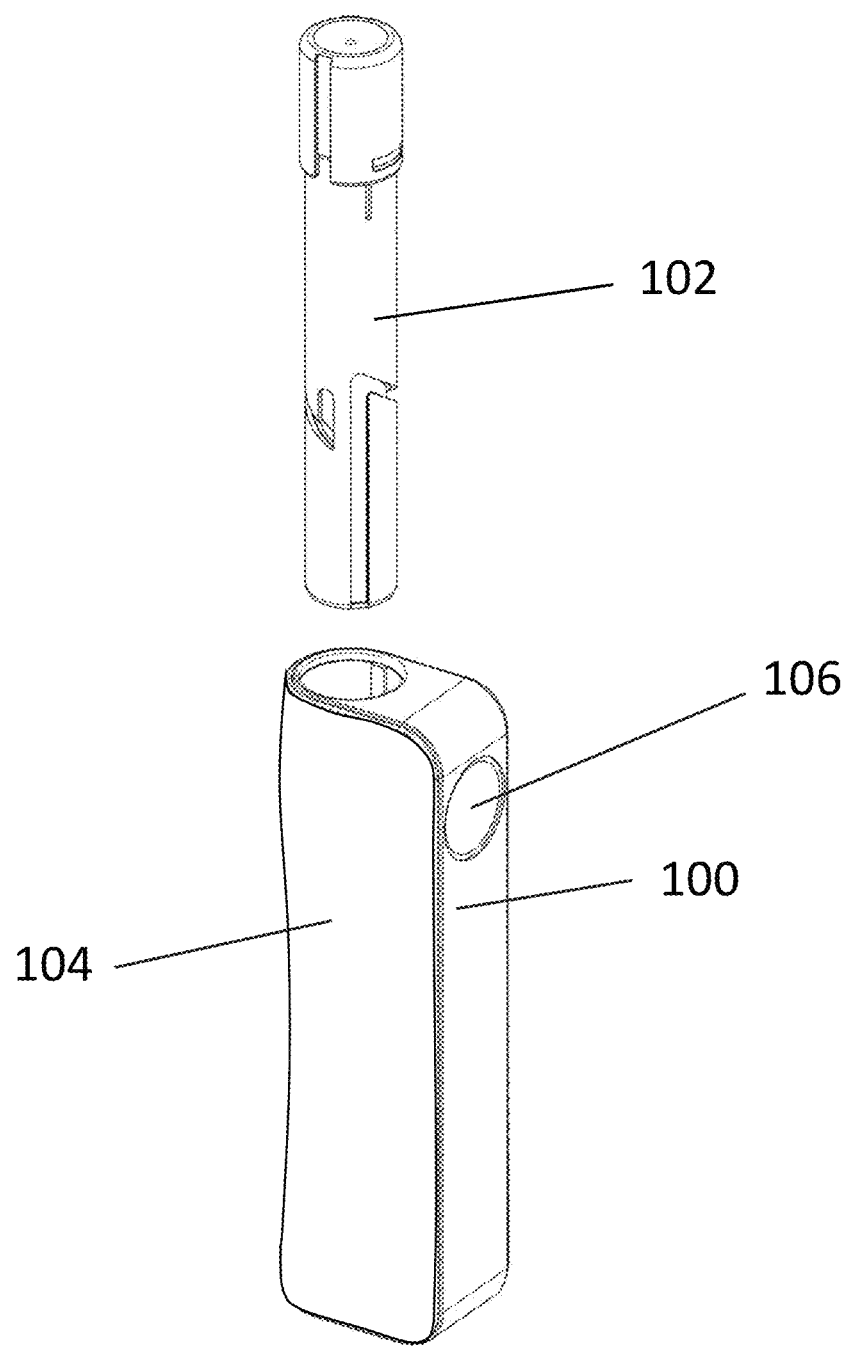
FIG. 1 shows an exemplary illustration a handheld medication dispensing device and associated medication cartridge according to various embodiments of the present invention.

The present invention relates to a medication dispensing system and, more particularly, to a caregiver system and method for interfacing with and controlling a medication dispensing device. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Principal Aspects

Various embodiments of the invention include three "principal" aspects. The first is a system (such as a patient system, caregiver system, or doctor portal system) for interfacing with and controlling a medication dispensing device. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

(2) Description

As noted above and as shown FIG. 15, the present disclosure provides a patient system 1500, caregiver system 1502, and doctor portal system 1506, that are designed to interface with and/or control a medication dispensing device 100 (e.g., oral medication spray device, etc.). The systems 1500, 1502, 1506 are implemented on external devices (e.g., mobile phone (wireless device), tablet computer, desktop computer, etc.) that include the programing and any other necessary information and/or components to allow for interfacing with and/or controlling the medication dispensing device 100. In some aspects, the patient, caregiver, and doctor portal systems 1500, 1502, and 1506 also include and/or share one or more remote servers 1504 (and associated processors) for storage and/or other operations as necessary to facilitate the system operations as listed herein. In some aspects, the remote server 1504 can also house or serve as a doctor portal system 1506 in which a doctor can access patient information that is shared or otherwise interfaced with the patient and caregiver systems 1500 and 1502. For clarity, the medication dispensing device 100 is described first, with the corresponding patient, caregiver, and doctor portal systems 1500, 1502, and 1506 described further below.

(2.1) Medication Dispensing Device

As noted above, one or more of the patient and caregivers systems 1500 and 1502 are configured to interface with a medication dispensing device, such as a handheld medication device 100 as depicted in FIG. 1. As shown in FIG. 1, the handheld medication dispensing device 100 is designed primarily to securely store and dispense medication from a medication cartridge 102. The device 100 comprises a housing 104, principally structured to protect the critical internal components while offering ergonomic suitability for handheld operation. The housing 104 exterior is designed with both convenience and comfort in mind, allowing a user to hold the device 100 and access the medication with ease. In an exemplary embodiment, the housing 104 may be configured in a variety of shapes, sizes, and materials to accommodate different user preferences and medication types.

In one aspect, the device 100 includes an authentication component 106 that is designed to authenticate a user's identification in various manners and, upon authentication, allow for operation and control of the device 100. The authentication component 106 is any suitable mechanism, device, system, etc., that allows for user authentication, non-limiting examples of which include a fingerprint reader built into the device 100 or facial recognition via a camera and app, etc. that communicates with the device 100 upon authentication to notify the device 100 of authentication and allow for operation of the device 100, or any other known authentication method or device. The authentication component 106 is set-up to permit the authenticated or designated user access to the operation of the said device 100, thereby ensuring a highly secure and personal way of dispensing medication. In one embodiment and as illustrated, the authentication component 106 includes a fingerprint reader and all associated components as necessary to allow for authentication with such a reader, including an integrated circuit, power source (battery), etc. For example, in a first use, the authentication component 106 can be configured to recognize the user and, thereafter, only allow access to the recognized user to cause the device 100 to operate as intended. Such a setup can be configured in any suitable manner as understood by those skilled in the art. As non-limiting example, a first use may require that a user turn on the device 100, which provides indicia (e.g., via a light, digital screen, etc.) to notify the user to place their finger on the fingerprint reader. The fingerprint reader then reads and stores the fingerprint of the designated user. Thereafter, the activator mechanism can only be activated by the designated user upon placement of the finger on the fingerprint reader. In another example, software or a phone application (i.e., the patient system) can be used to wirelessly communicate (e.g., via Wi-Fi, Bluetooth, etc.) with the device 100 to program the device 100 to only recognize the designated user via the authentication component 106. Thus, the dispensing device 100 includes all necessary components to allow it to wirelessly communicate with an external device, non-limiting examples of which include Wi-Fi transceivers/components, Bluetooth components/gear, etc. In an alternative embodiment, the device 100 can simply be turned off and on and includes a button or other similar feature to cause the device 100 to operate and actuate the activator mechanism after user authentication.

In another embodiment and in the case of facial recognition via a camera and app, etc. on a mobile phone that communicates with the device 100, the authentication component 106 includes components housed within device 100 to allow for remote authentication, including the programming on an integrated circuit or similar device, along with the wireless communication components necessary to communication with the mobile phone (e.g., Bluetooth, WiFi transceivers, etc.) to allow for authentication and operation of the device 100. The software or application that is downloaded onto the mobile phone or device includes the programing and any other necessary information to allow for user authentication and cause the authentication to be transmitted and received by the authentication component 106.

In one aspect, the authentication component 106 is a biometric fingerprint reader linked to a mobile app, which can be used to prevent unauthorized medication dispensing, requiring user authorization via the app for initialization, and connecting to caregivers and personal networks to ensure medication adherence. The design of the device 100, accessories, and app is centered around the need for an easier and better way to receive the right dose, at the right time, in the right way and frequency. In one aspect, controlled via the app, the handheld device 100 can alert users to their medication schedule, while also notifying caregivers and family members about adherence. For restricted medications, the device 100 and associated app can restrict dosing until authorized by the prescribing physician. Tampering with the medication cartridge 102 triggers alerts to caregivers, pharmacists, and physicians, ensuring safe usage, especially for restricted medications by alerting through the app that the medication has not been taken as prescribed. In another aspect, the device 100 and medication cartridge 102 are formed to include any necessary components that allow the device 100 to recognize a specific medication cartridge 102. As a non-limiting example, each medication cartridge 102 can be formed to include a Radio Frequency Identification (RFID) tag, while the device 100 includes an RFID reader (or other similar technology).

Figure 15:
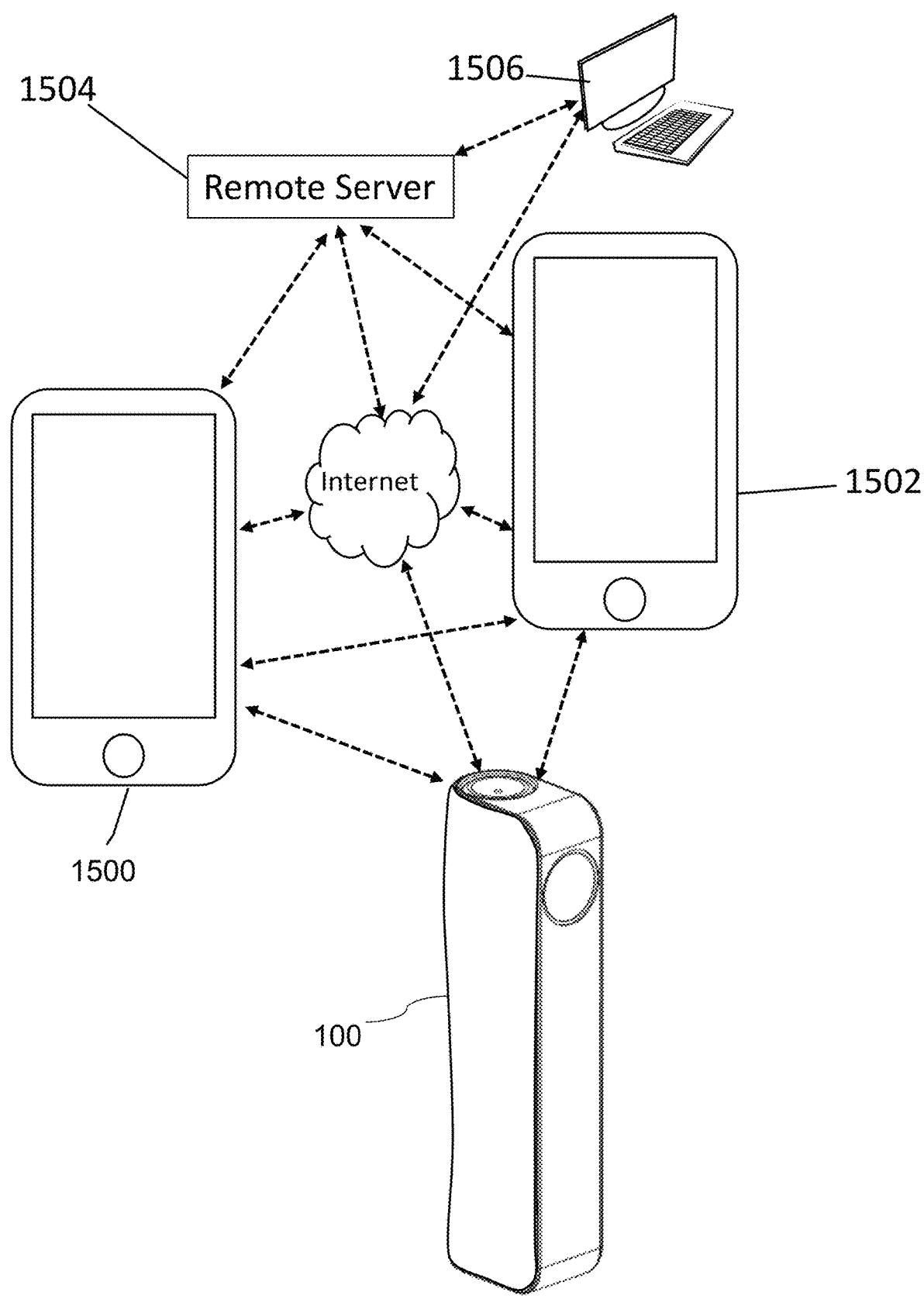
FIG. 15 is a block diagram depicting control of a dispensing device according to various embodiments of the present invention.

As noted above, the device 100 is formed to wirelessly communicate with a system (i.e., as shown in FIG. 15, an external device (e.g., mobile phone) and its app) to allow for the system (e.g., external device) to control one or more features as applicable to the device 100. In doing so, the dispensing device 100 includes a wireless communication component (depicted as element 202 in FIG. 2) which include all necessary components to allow it to wirelessly communicate with the external device and control the dispensing device 100 to provide the desired operations, non-limiting examples of which include Wi-Fi transceivers/components, Bluetooth components/gear (e.g., a system on a chip (SoC) that includes a transceiver, antenna and control chip), integrated circuit(s), a power source (e.g., battery), and/or any another other electronic components as may be needed to allow for wireless or Bluetooth connectivity and related operations of the device 100. In one aspect and per Bluetooth protocol, when the dispensing device 100 links with the associated system (e.g., mobile external device as shown in FIG. 15) to communicate, they form an ad hoc mini computer network referred to as a piconet. Within the piconet, the external device, referred to as the master, assumes the control of the network, issuing instructions to the dispensing device 100, which is referred to as a slave to control a variety of features and operations.

As noted above, several programmable features include controlling user access and operation of the device 100 (and activator mechanism, etc.) based on user authentication, dosing schedules, restricting dosing until authorized by a prescribing physician, etc. As a non-limiting example, after a medication cartridge 102 is inserted into the device 100, it is essentially locked and not allowed to position the medication cartridge 102 into the dispensing position until access is granted. This access can be based on the mobile phone user authentication process which transmits an "access granted" signal (via Bluetooth, etc.) to the device 100 and allows the activator mechanism (described in further detail below) to operate and move the medication cartridge 102 to the dispensing position. Without such an "access granted" signal that is wirelessly received by the dispensing device 100, the device 100 is locked and will not activate the activator mechanism. As yet another non-limiting example, the dosing schedule as recorded into the software application and external device may specify that the medication is be dispensed a certain number of times daily. A user would then connect their mobile external device (e.g., mobile phone) via Bluetooth to the dispensing device 100 during the allotted times, at which point an "access granted" signal is provided to the dispensing device 100. The software application as stored in the mobile external device will only provide the "access granted" signal that corresponds to the dosing schedule, while the dispensing device 100 is locked or deactivated during all other times. In other words and as can be appreciated by those skilled in the art, there are a variety of features of the dispensing device 100 that can be operated by providing the wireless communication components that allow for wireless control of the dispensing device 100 via a mobile phone or other external wireless device.

As shown in the interior views of FIGS. 2A and 2B, integrated within the housing 104 is a cartridge carrier 200. The cartridge carrier 200 functions as a receptacle for the medication cartridge 102. The cartridge carrier 200 includes a keyed connector, most importantly, innovatively designed to align with a specified type of medication cartridge 102. This keyed connector serves as an interlocking structure that carefully guides the positioning and orientation of the cartridge 102, allowing only for the insertion of a compatible medication cartridge 102. The keyed connector along with the cartridge carrier 200 ensure the correct placement and alignment of the medication cartridge 102, which can help eliminate potential misuse or cartridge damage, and fostering a smooth transition between stored and dispensing positions (as described in further detail below).

Figure 3:
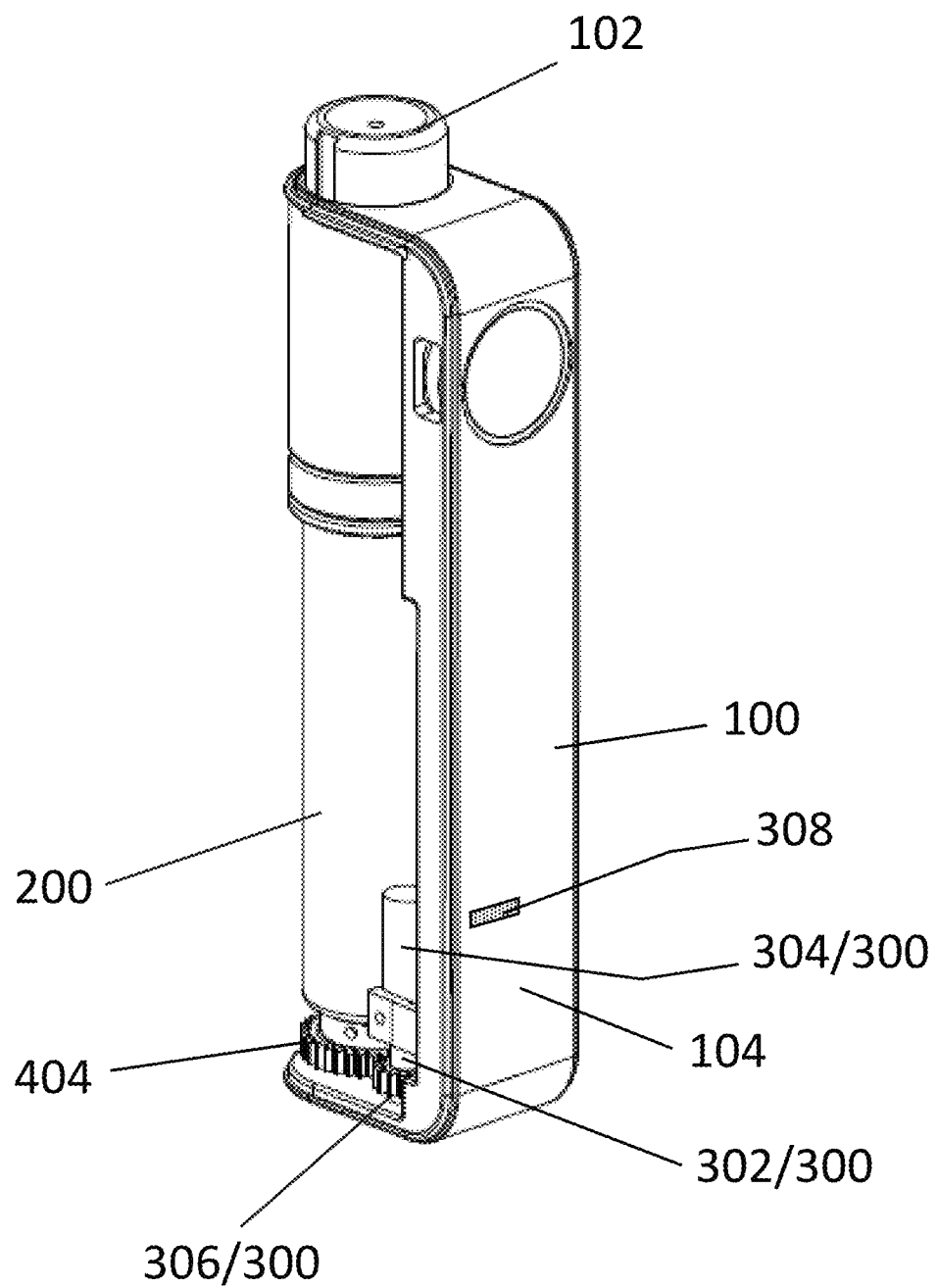
FIG. 3 is an interior-view illustration of the medication dispensing device, depicting an activator mechanism as operably connected with the cartridge carrier.

As shown in the interior view of FIG. 3, an activator mechanism 300 forms part of the configuration and is integrated within the housing 104. The activator mechanism 300, when engaged or otherwise activated, prompts the cartridge carrier 200 to actuate. The involvement of the activator mechanism 300 ensures a controlled movement of the inserted medication cartridge 102 between at least two positions-a stored position and a dispensing position. Note that FIG. 2A depicts the medication cartridge in a stored position, while FIG. 3 depicts the medication cartridge in a dispensing position.

In the stored position, as shown in FIG. 2A, the medication is kept secure within the device 100. The position ensures safety by preventing unintentional discharge of medication when not in use. When the activator mechanism 300 is activated, the cartridge carrier 200 rotates to lift up the medication cartridge 102 into the dispensing position. When this dispensing position is selected, the medication cartridge 102 is correctly oriented to dispense the medication through a dispensing aperture (described in further detail below) integrated into the medication cartridge 102.

The link between the activator mechanism 300 and the cartridge carrier 200 allows for reliable and essential movement control. This means the user can confidently operate the device 100 knowing the medication is dispensed accurately and safely.

The cartridge carrier 200 is formed in any suitable manner to allow for activation by the activator mechanism 300, which results in transitioning the medication cartridge 102 between the stored and dispensing positions. In an embodiment and as shown in FIG. 3, the cartridge carrier 200 is rotatable within the housing 104. The cartridge carrier 200 may be formed of materials that possess strength and durability such as, but not limited to, metals, polymers, and/or composites. The size, shape, and dimensions of the cartridge carrier may vary as per the application requirements.

The housing 104 may be constructed to accommodate the rotatable cartridge carrier 200. The construction of the housing 104 can also encompass different types of materials that provide the necessary strength and durability inclusive of, but not limited to metals, polymers, composites, among others. The interior of the housing 104 is ideally designed to allow the cartridge carrier 200 to rotate through actuation of the activator mechanism 300.

The activator mechanism 300, ensuring the cartridge carrier's 200 rotation within the housing 104, can be implemented through a variety of means, such as mechanical gears, electric motors, a battery, manually operated mechanisms, integrated circuits, or any combination thereof. This activator mechanism 300 administration permits the user to precisely position the cartridge carrier 200 within the housing 104 between a first position (in which the medication cartridge 102 is inserted into the cartridge carrier 200 and is stored in a stored position) and a second position (in which the medication cartridge 102 is lifted from the housing 104 to a dispensing position). The activator mechanism 300 can then be activated to rotate the cartridge carrier 200 in an opposite direction to return the medication cartridge 102 to the stored position.

In one aspect, the dispensing device 100 includes a locking mechanism that is configured to selectively lock/unlock the mediation cartridge 102 within the cartridge carrier 200. The locking mechanism may involve an interlocking system, a magnetic attachment, or any other secure attachment mechanism. As a non-limiting example, the locking mechanism may be a spring-loaded detent style 'click-in' and 'click-out' mechanism formed at the bottom of the medication cartridge 102 and cartridge carrier 200. In another aspect, the locking mechanism can be an electronically actuated lock (e.g., mechanized tab, etc.) that locks the medication cartridge 102 into the cartridge carrier 200. For example, the exterior surface of the medication cartridge can include a slot that is formed to accommodate a tab that is electronically moved (e.g., turned/slid, etc.) into the slot when locking and, in the alternative, pulled from the slot when released. As yet another non-limiting example, the locking mechanism can include programming such that after the cartridge 102 is inserted into the cartridge carrier 202, the cartridge carrier 200 is rotate partially until alignment features (described in further detail below and depicted as element 406) are positioned in the middle of the second slot (described in further detail below and depicted as element 710), with the cartridge carrier 200 then stopped until it is desired to rotate further to position the medication cartridge 102 in the dispensing position. With the alignment features in the middle of the second slot, the cartridge 102 is effectively locked within the cartridge carrier 200. Thus, as can be appreciated by those skilled in the art, there are several mechanisms that can be employed to selectively lock the medication cartridge 102 into the cartridge carrier 200.

In another aspect, the inclusion of the locking mechanism may also be included to secure the cartridge carrier 200 at any desired rotational position, thus preventing unintentional and unwanted movement when the cartridge carrier 200 is set in a particular position. This locking mechanism can be integrated into the cartridge carrier 200, the housing 104, the activator mechanism 300, or combinations of these components. This rotatable cartridge carrier 200 system installed within a housing 104 assembly may have wide ranging applications, such as, for instance, accommodating various cartridges for providing users with quick and easy access to different medications and dosages, multiple configurations, interchangeability of components, and more. Thus, the present one embodiment discloses a rotatable cartridge carrier 200, promoting ease of use, enhancing performance, providing efficient operation, flexibility, improved control and precision, leading to a more efficient and user-friendly functionality.

Figure 4:
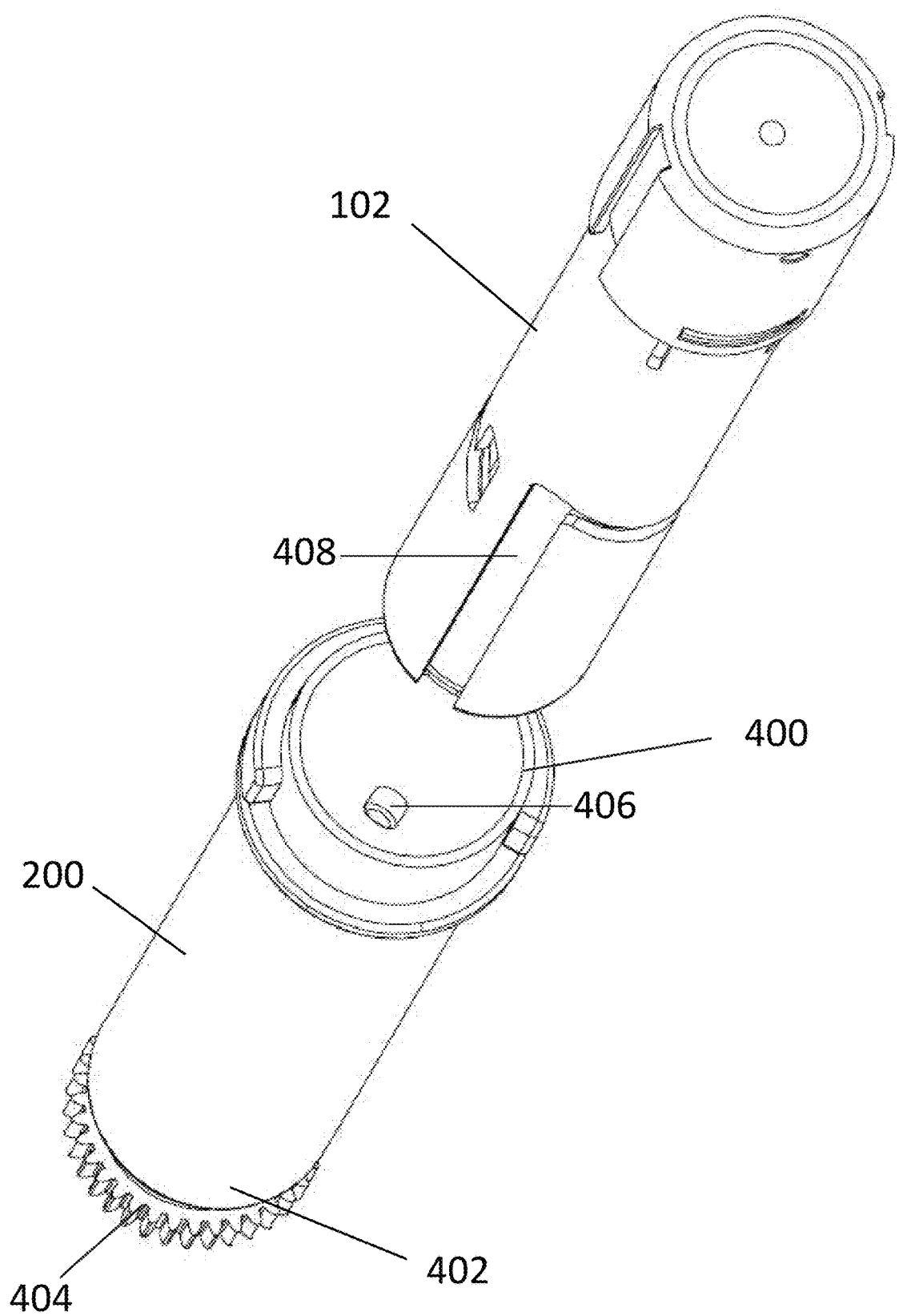
FIG. 4 shows an exemplary illustration of the cartridge carrier and medication cartridge.

In one embodiment and as shown in FIG. 4, the cartridge carrier 200 includes both a proximal end 400 and a distal end 402. The proximal end 400 of this unit is open, and it is specifically structured to receive the medication cartridge 102. This can be any kind of medication cartridge 102, and the open design simplifies the process of interchanging cartridges of differing medications, volumes, or other specifications, thus making it broadly applicable and versatile.

The distal end 402 of the cartridge carrier 200 includes a key component of this one embodiment-a gear wheel 404. This gear wheel 404 is not a mere inclusion but is operably connected to the activator mechanism 300. The gear wheel 404 and activator mechanism 300 are conceptually designed to work in harmony. In operation, when the user deploys the activator mechanism 300, the included gear wheel 404 is rotated, thereby rotating the cartridge carrier 200.

The gear wheel 404 is a significant element in the functioning of this device 100 mainly due to its interaction with the activator mechanism 300. The gear wheel 404, upon the interaction with activator mechanism 300, contributes to the precision with which the cartridge carrier 200 is rotated to position the medication cartridge 102 between the stored and dispensing positions. Its size, teeth count, and interaction with other gears if connected, contribute to its function.

Moreover, the position of the gear wheel 404 at the distal end 402 of the cartridge carrier 200 may also assist in a user-friendly, ergonomic design. The gear wheel's 404 location ensures a seamless connection between the mechanical parts of the activator mechanism 300 and the carrier cartridge 200, augmenting the device's 100 overall performance.

As noted above and referring again to FIG. 3, the device 100 includes an activator mechanism 300 to selectively turn the gear wheel 404 and, by extension, rotate the cartridge carrier 200. The activator mechanism 300 includes any components as necessary to rotate the gear wheel 404. In one embodiment, the activator mechanism 300 comprises of at least a power source (e.g., battery 304), a motor 302, and one or more gears 306 that are operably connected to the gear wheel 404. The battery 304 in the device 100 forms the power source, capable of providing a stable and reliable supply of power to the other components. The size, capacity, and type of the battery 304 may be customized according to design preferences, device requirements, or various other factors, while being compliant with standard safety and operation guidelines. In some aspects, the battery 304 is encased within the device 100 and intended for device 100 replacement upon depletion of the battery 304, while in other aspects, it is replaceable. In yet other aspects, the battery 304 is rechargeable using a charging port 308 or any other charging means as known to those skilled in the art.

The motor 302 functions as the primary mechanical component that is responsible for movement or force in the device 100. Upon activation, the motor 302 draws power from the battery and begins to turn to rotate any of the one or more gears and the operably connected gear wheel 404. The type, size, and characteristics of the motor 302 can be adjusted based on the requirements of the device, anticipated load, desired performance factors among other parameters.

The one or more gears represent a transmission mechanism, operably connected to the motor 302 and the gear wheel 404. Upon the activation of the device 100, the rotational force produced by the motor 302 is transferred to these gears. The gears enable the transfer of power from the motor 302 to the gear wheel 404. Upon receiving the force from the one or more gears of the activator mechanism 300, the gear wheel 404 begins to turn. This turning of the gear wheel 404 then contributes to the rotation of a cartridge carrier 200.

Referring again to FIG. 4, one embodiment pertains to an enhanced cartridge carrier 200, specifically designed with one or more alignment features 406 that protrude into the cartridge carrier 200 for a keyed connection and accurate cartridge 102 positioning, thereby improving the overall functionality of the cartridge 102 and the cartridge carrier 200.

The alignment features 406 of one embodiment are distinguishable protrusions present on the inner surface of the cartridge carrier 200. These alignment features 406 serve to guide the cartridge 102 into the correct position within the cartridge carrier 200 when installing a cartridge 102 into the cartridge carrier 200. These protruding alignment features 406 also help to prevent misalignment and displacement of the cartridge 102 while it is installed and during operation. Notably and as described below in further detail, the alignment features 406 are critical in transitioning an inserted cartridge 102 between the stored and dispensing position.

The alignment features 406 are strategically located within the cartridge carrier 200 in a manner to engage with corresponding features or portions on the cartridge 102. When the cartridge 102 is inserted into the carrier 200, the protruding alignment features 406 guide it into the correct position as the features 406 fit into compatible sections (i.e., alignment channels 408) of the cartridge 102. This results in a snug and correct fit of the cartridge 102 within the cartridge carrier 200.

Furthermore, these alignment features 406 may come in various shapes and sizes and can be constructed using various materials that are suitable for the device and the intended application. They can be rigid to withstand the pressure exerted by the cartridge 102 as it is inserted into the cartridge carrier 200, or flexible to allow for slight variations in cartridge 102 size and shape.

For further understanding, FIGS. 5A through 5C depict side, top, and cross-sectional views, respectively, of the cartridge carrier 200 and alignment features 406. These features 406, protruding into the interior of the cartridge carrier 200, support the accurate placement of cartridges 102 within the device. Thus, the functionality and efficiency of the overall dispensing device 100 are significantly improved along with consistent cartridge 102 performance ensured by these alignment features 406. This inventive cartridge carrier 200 design genuinely adds value to applications where precise alignment of cartridges 102 is crucial. This one embodiment indeed ensures an innovative update for improving the efficiency of cartridge insertion and alignment in a cartridge carrier, potentially paving the way for advancements in devices utilizing such cartridge carriers.

As noted above and referring again to FIG. 4, the present disclosure also provides a unique medication cartridge 102 that can be inserted within a cartridge carrier, thus providing a novel means to carry, store and administer medication. The essence of this one embodiment lies in the exclusive design of the medication cartridge 102 and the cartridge carrier that is not only easy to operate but also provides secure storage and effortless administration of the medication.

The medication cartridge 102 is an integral part of the inventive concept and is designed to contain distinct types of medications, be it in liquid, gel, or cream, or other dispensable forms of medication. The cartridge 102 can be made up of pharmaceutically safe materials ensuring no chemical reactions occur when in contact with the medication. The cartridge 102 itself can showcase cylindrical or other geometrical shapes as required by shape of the cartridge carrier 200. The medication cartridge 102 and cartridge carrier 200 partnership provides an ideal solution in various medical environments, such as hospitals, pharmacies, nursing homes, or even domestic settings. It proves to be beneficial where multiple medications should be stored and administered safely and hygienically. It combines innovation with convenience, improving medication storage, and administration methodologies.

As noted above and as shown in FIG. 6, the cartridge 102 itself is also designed to provide a marked improvement over other medication containers. It is envisioned to include markings or identification systems for easily recognizing the type of medication stored within each cartridge 102. The real innovation lies in the incorporation of one or more channels 408 and aligned slots 606 within the cartridge 102. These are constructed meticulously within the cartridge 102 and serve a distinct function of aligning and receiving one or more alignment features 406. As will be evident below, these channels 408 and slots 606 engage with the aforementioned alignment features 406 to allow for controlled operation of the device 100.

Figure 6:
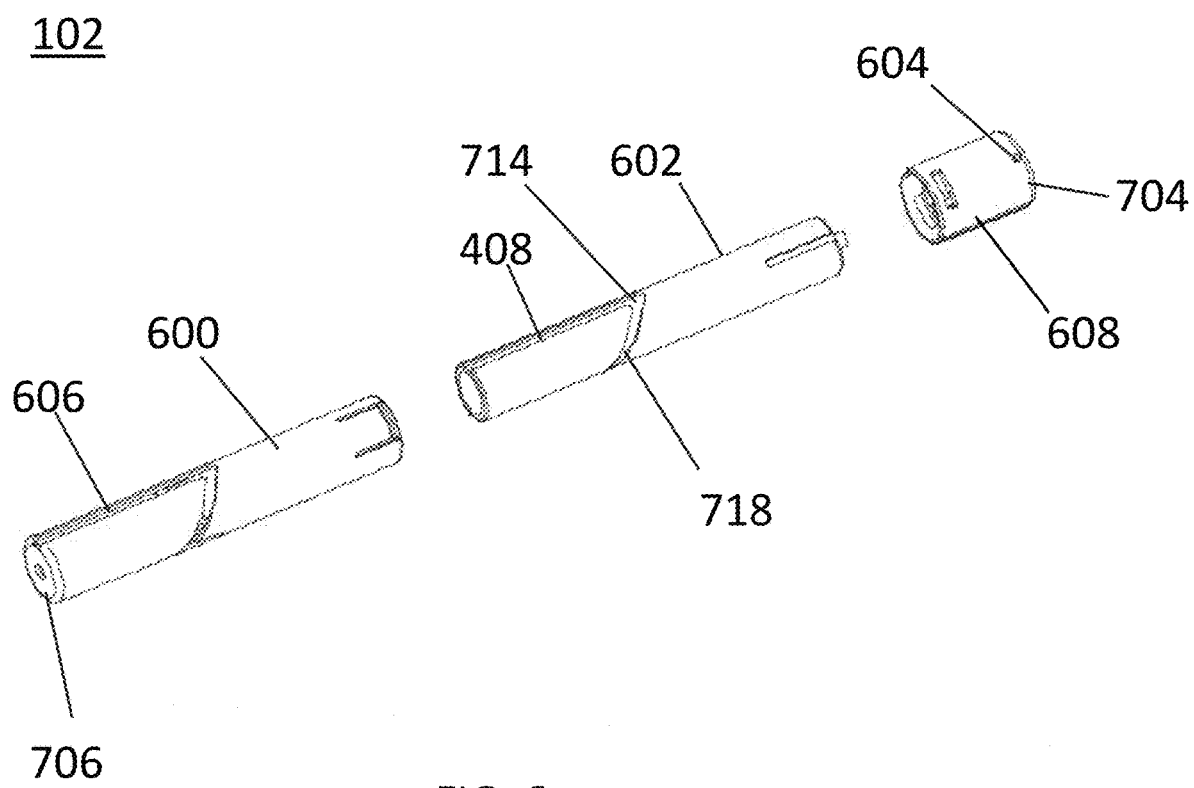
FIG. 6 shows an exploded-view illustration of the medication cartridge.
Figure 7A:
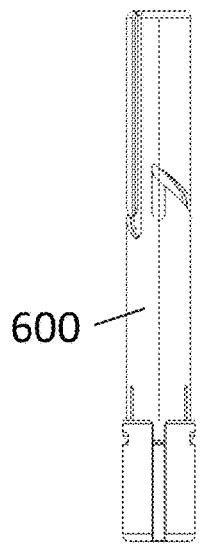
FIG. 7A shows a front-view illustration of the medication cartridge.
Figure 7F:
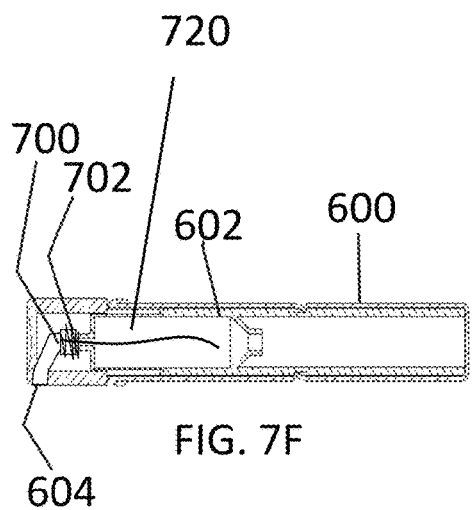
FIG. 7F is a cross-sectional, side-view illustration of the medication cartridge, taken from line A-A of FIG. 7C.
Figure 7B:
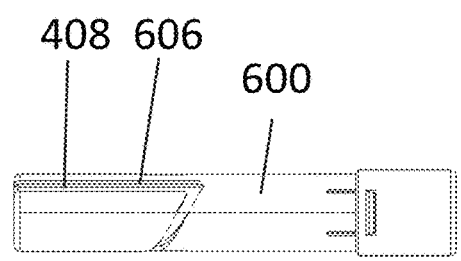
FIG. 7B shows a right, side-view illustration of the medication cartridge.
Figure 7E:
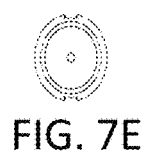
FIG. 7E shows a top-view illustration of the medication cartridge.
Figure 7C:
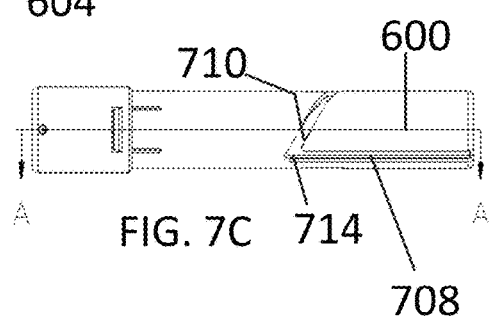
FIG. 7C shows a left, side-view illustration of the medication cartridge.
Figure 7D:
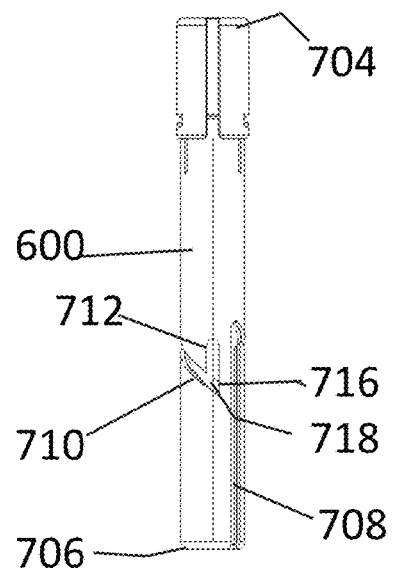
FIG. 7D shows a rear-view illustration of the medication cartridge.

Further and as shown throughout FIGS. 6 through 7F, the present disclosure provides an improved configuration for a medication cartridge 102, particularly advantageous for medications that require enhanced storage for securely maintaining their efficacy and quality. The innovative design of the medication cartridge 102 includes a robust shell 600 that has a dispensing aperture 604 designed for the release of the medication stored within a medication vial 602.

The shell 600, formed from long-lasting and reliable material (e.g., plastic, metal, etc.), is shaped to house the vial 602 securely and efficiently. This shell 600 acts as a protective layer for the vial 602 placed inside, while maintaining the required conditions for the preservation of the medication. The dispensing aperture 604 deployed on the shell 600 is engineered in a way to align with the outlet 702 of the vial 602, ensuring precise and mess-free dispensation of the medication.

Inside the shell 600 is a medication vial 602, which is shaped and positioned in a manner that it can slide without difficulty within the shell 600. This ability of the vial 602 to slide enables convenient load and unload of the medication. The vial 602 includes a pump assembly 700 that is equipped with an outlet 702. The design and positioning of this outlet 702 are such that it aligns perfectly with the dispensing aperture 604 on the shell.

Figure 7G:
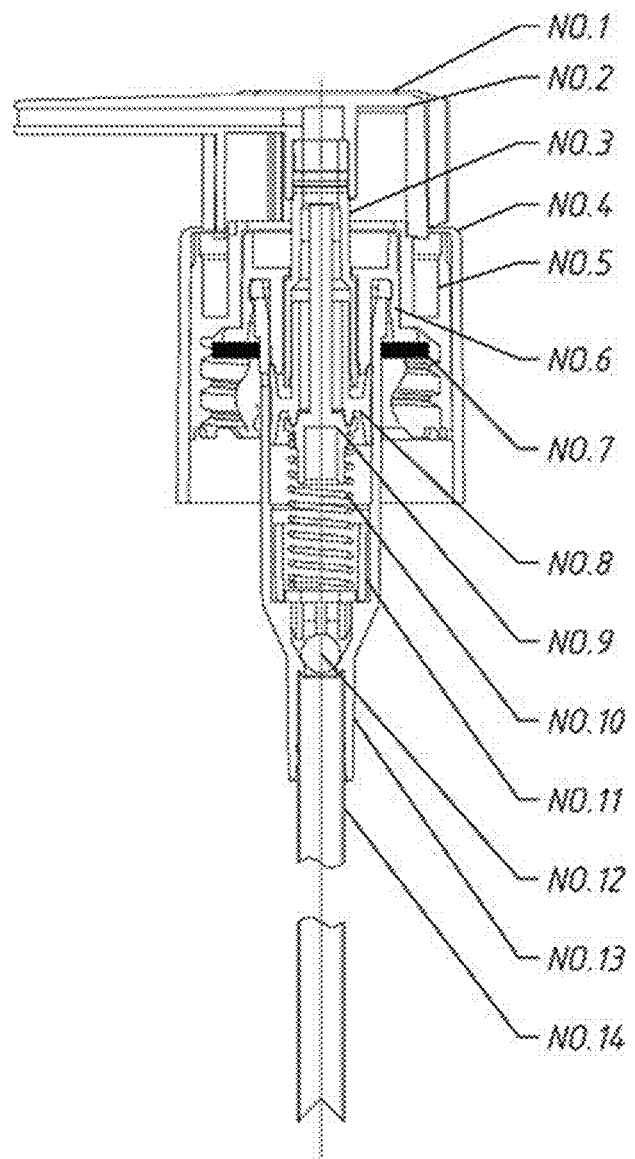
FIG. 7G is an illustration of a lotion pump assembly of the prior art.
Figure 7H:
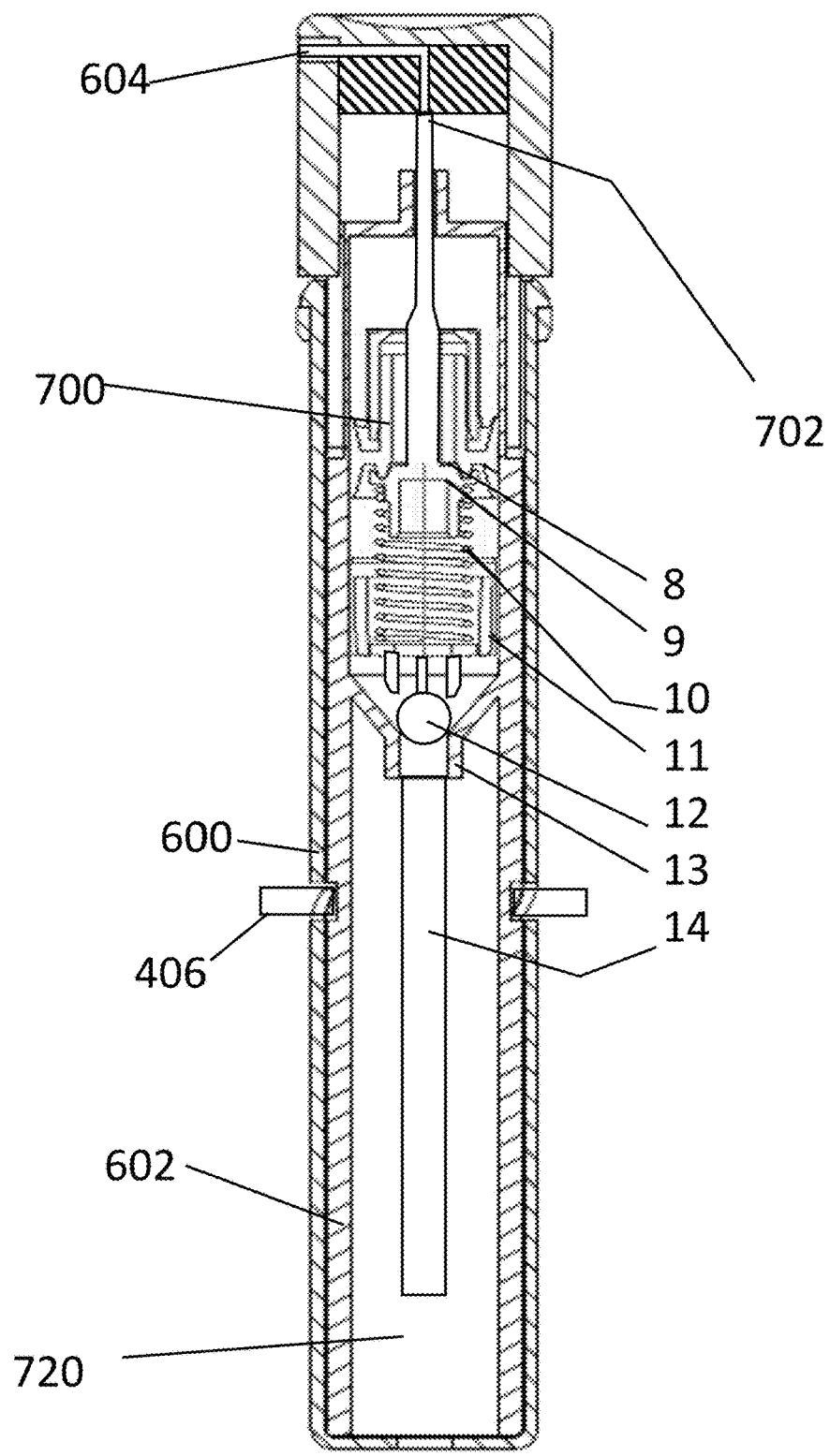
FIG. 7H is an illustration of an example pump assembly as applied to the medication cartridge in accordance with various embodiments of the present invention.

The pump assembly 700 is any suitable assembly that can be affixed with a container (i.e., the vial 602) to allow for pumping or otherwise dispensing a medication or fluid therefrom, a non-limiting example of which includes a compression or spring-loaded pump, similar to the pump mechanism as used in a standard lotion bottle. For reference, FIG. 7G provides an illustration of an example pump assembly as provided for in the prior art, while FIG. 7H provides a non-limiting example of the pump assembly as modified and applied to the present invention. The pump assembly of the prior art (as shown in FIG. 7G) includes a clamp 1, press head 2, press lever 3, coat 4, screw cap 5, connect cap 6, gasket 7, piston 8, piston seat 9, spring 10, spring seat 11, valve 12, housing 13, and a straw 14. As applied to the present invention (as depicted in FIGS. 7F and 7H), the pump assembly 700 is connected to the vial 602, while the shell 602 serves as the press head that is used to press down the piston 8 to force the fluid through the straw 14 and out of the dispensing aperture 604. In some instances the pump assembly 700 can be screwed onto the vial 602; however, it should be understood that the invention is not intended to be limited thereto as the pump assembly 700 can be attached in any suitable manner between the vial 602 and shell 600 to allow for dispensing fluid from the vial 602 and out of the dispensing aperture 604. Further, it should be understood that the specific pump assembly 700 as depicted in FIG. 7H is provided as a non-limiting example of a suitable pump assembly and that the invention is not intended to be limited thereto as other mechanisms or assemblies can be used to dispense the fluid upon actuation. For example, the pump assembly can be formed as an airless pump, a peristaltic pump, a diaphragm pump, a pressurized canister style pump, or any other configuration in which activation of the assembly causes the fluid to dispense.

For illustrative purposes in comparison to a lotion bottle, the vial 602 would serve as the container to hold the fluid, while the shell 600 serves as the pump head that can be depressed to pump the fluid, with the various components of the pump assembly 700 positioned therebetween. In operation and when the medication cartridge 102 is moved to the dispensing position, the alignment features 406 operate to hold the vial 602 in place (due to their locking position in the channel terminal as described in further detail below), while a user can selective press the shell 600 downward around the vial 602 to activate the pump assembly 700 and force fluid from the vial 602.

For example, the vial 602 includes a reservoir 720 in which the medication is stored. The medication can be in a gas or fluid form; however, desirably and in one aspect, the medication is fluid and can be squirted from the medication cartridge 102 (and vial 602) via actuation of the pump assembly 700. As apparent from the description further below, the pump assembly 700 can be easily operated to cause the medication to be dispensed from the vial 602 through its outlet 702. When a force is applied on the pump assembly 700, it triggers the release of the medication inside of the vial 602, causing the medication to travel from the vial 602, passing through the aligned outlet 702 and dispensing aperture 604, where it is released to the user.

As noted above, the pump assembly 700 is any suitable assembly, mechanism, or device that can be affixed with the vial 602 to allow for selective dispensing therefrom. As can be appreciated by those skilled in the art, a non-limiting example of such a pump assembly 700 is a spring-loaded assembly utilizing a stacked one-way valve setup to temporarily create a vacuum, allowing fluid to be aspirated from the reservoir 720 and dispensed through the outlet 702 and dispensing aperture 604 upon depression of the shell 600 around the vial 602.

As noted above, the medication cartridge 102 is generally formed of two components, a shell 600 and a medication vial 602. The vial 602 is sized to be secured within and slide within the shell 600. As shown, the medication cartridge 102 includes a top end 704 and a bottom end 706. Although the shell 600 in FIG. 6 is illustrated as having a cap component 608 at the top end 704, the invention is not intended to be limited thereto as the shell 600 can be formed such that the cap component 608 is integrally formed with the shell 600 as a single unit. In such an aspect, a hole (e.g., sealable hole) can be formed at the bottom end 706 (or top end 704) of the shell 600 to allow for insertion of the vial 602 into the shell 600.

Notably and of particular importance, the vial 602 includes channels 408 that are aligned with the slots 606 on the shell 600. These channels 408 and slots 606 are built in a manner to accurately align with the alignment features 406 of the cartridge carrier 200. The number and size of these channels 408 and slots 606 can vary depending on the number of alignment features 406 intended to be placed therein. These channels are purposefully built to receive these alignment features, allowing secure and precise positioning. This design ensures that the alignment features do not shift their placement, further guaranteeing the stabilization of the medication within the cartridge.

For example, one example embodiment includes a structure involving a pair of opposing channels 408 are formed on opposite sides of the vial 602. These channels 408 are typically parallel to each other, though variations can occur. In one aspect, each of the pair of opposing channels 408 originates from the lowermost end or bottom end 706 of the vial 602. The pair of opposing channels 408 rise upward from this point, extending towards the top end 704 of the vial 602. This ascension continues until they reach a point known as the first junction 714. It must be clarified that this first junction 714 is not an arbitrary point but is a strategically designed and located structural feature within the device to precisely position the cartridge 102 between stored and dispensing positions.

Once these channels 408 have reached the first junction 714, the trajectory shifts. At this point, the channels 408 do not continue with the upward gradient. Instead, they commence a downward traversal toward the bottom end 706. They proceed downwards, but not vertically downwards. This descent is carried out on an angle around the vial 602, intended to enhance function and performance.

These angled downward channels 408 continue to move in the said direction until they reach an area deemed as the second junction 716. It is at this point that these channels 408 cease to continue. They terminate at this juncture, each channel 408 ending in what is referred to as a channel terminal 718. As will be apparent below, this distinctive configuration of the channels 708 enables them to perform their intended purpose more efficiently. It is important to consider the precise and specific architectural design of these channels 408, including their starting point at the bottom end 706 of the vial 602, their rise towards the first junction 714, their angled descent towards the second junction 716, which with respect to the channels, is the final termination at the channel terminal 718. These particular design elements reveal a thoughtful consideration of their role within the device and contribute both independently and collectively to the overall functionality and performance of the device or assembly in question.

The present disclosure also provides an embodiment which is characterized by a pair of opposing slots 606 in the shell 600 that align with the pair of opposing channels 408. More specifically, one embodiment is the configuration and interaction of these parts, enabling the pair of opposing protrusions 406 to pass through the pair of opposing slots 606 and into the pair of opposing channels 408 to allow for moving the cartridge 102 between the stored and dispensing positioned and, ultimately, sliding the vial 602 within the shell 600 for dispensation of the medication.

The pair of opposing slots 606 are formed through the surface of the shell 600 to allow access to the channels 408 therein. These slots 606 are designed with precise measurements to fit and accommodate corresponding elements, namely, a distinct pair of opposing protrusions 406. The opposing slots 606 are carved or formed into the shell 600 and aligned in such a way that they maintain a clear, unobstructed path for the protrusions 406 to pass through them with ease. The unique arrangement allows for the insertion of the pair of opposing protrusions 406, which are another critical characteristic of this one embodiment. These protrusions 406, with their matching dimensions to the slots 606, are designed to glide smoothly through the opposing slots 606 and into the aligned opposing channels 408. The path provided by the slots 606 guides and directs the protrusions 406 into the appropriate channels 408. Consequently, this ensures a specific interaction between the three parts: the opposing protrusions 406 smoothly pass through the opposing slots 606, and they are then guided into the opposing channels 408, maintaining a suitable and secure connection.

Further, the medication cartridge 102 presents an innovative design with respect to the pair of opposing slots 606. Each of the pair of opposing slots 606 is formed of a first slot 708, a second slot 710, and a third slot 712. These slots are strategically positioned and oriented for the optimal functioning of the device. The first slot 708 in each pair begins at the bottom end 706 of the shell 600 and extends upward toward the top end 704. It is arranged in such a way that it mandates a route which ascends from the base to a designated position along the length of the cartridge 102, otherwise referred to as the first junction 714.

Subsequent to the first junction 714, the structure of the shell 600 features a second slot 710 for each pair. Instead of following the upward trajectory of its predecessor, this second slot 710 takes on a unique characteristic of its own by providing an angled path that descends from the first junction 714. This downward movement proceeds until it reaches a designated point along the body of the shell 600, referred to herein as the second junction 716. Moreover, the slot design of the shell 600 reverts back to an upward direction in the subsequent and final arrangement of each pair—the third slot 712. Commencing from the second junction 716, this slot ascends once again (e.g., vertically) towards the top end 704 of the cartridge. The distinct positions and paths of the slots 708, 710, and 712 provide a sophisticated layout that enhances the fundamental operations of this medication cartridge 102. Notably, while the channel 408 terminates at the second junction 716 or channel terminal 718, the third slot 712 proceeds upwards from the second junction 716. This differentiation allows for the selective dispensing of the medication therein. This innovative structure enhances the controlled dispensing of medication, making this cartridge 102 particularly advantageous in the administration of drugs. The angles and special slot layout improves the overall efficiency and operational effectiveness of the delivery device, which in turn can broaden its potential applications in the medical and pharmaceutical fields. The precise orientation of the slots from bottom to top and their alternating directions contribute to creating a balanced and smooth transition of the medication within the cartridge 102. The level of control provided by this inventive structure is a significant evolution in medication delivery designs.

Figure 8A:
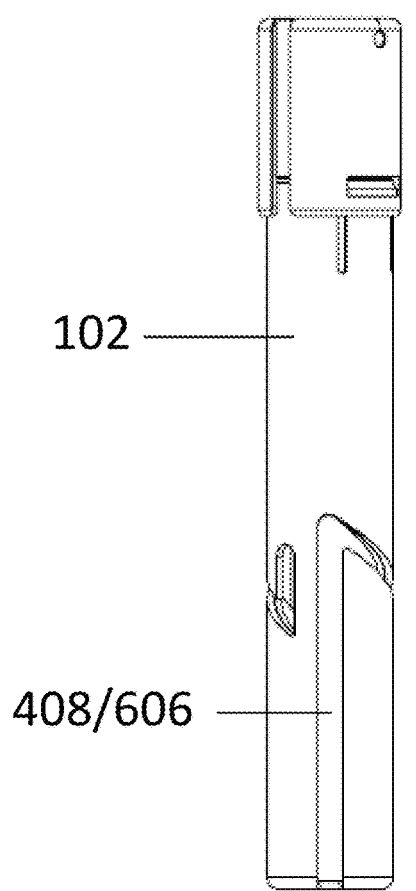
FIG. 8A shows an exemplary illustration of the cartridge carrier and medication cartridge.
Figure 8B:
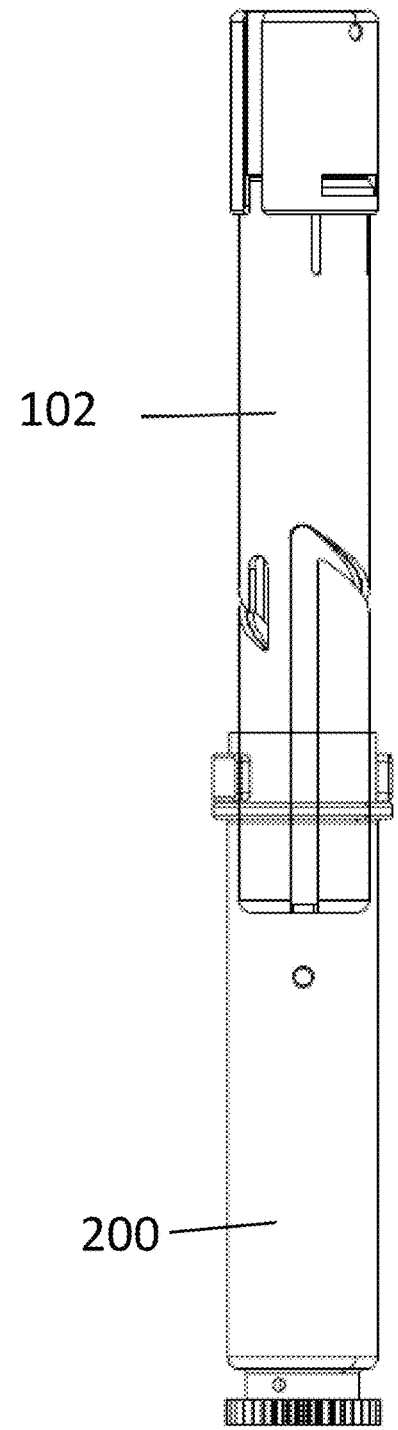
FIG. 8B shows an exemplary illustration of the cartridge carrier and medication cartridge, depicting the medication cartridge as being inserted into the cartridge carrier.
Figure 9:
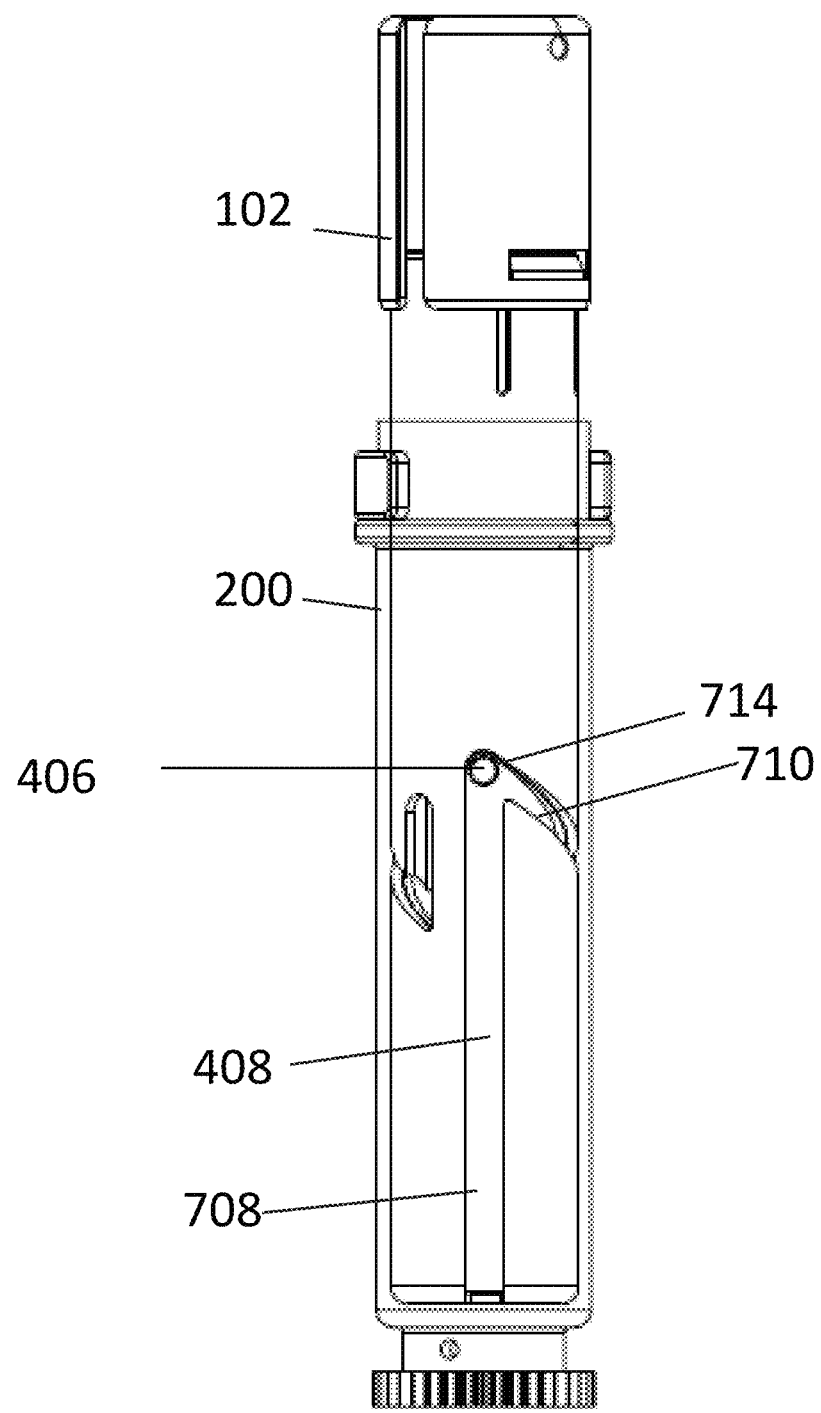
FIG. 9 shows an exemplary illustration of the medication cartridge inserted into the cartridge carrier.

For further understanding, FIGS. 8A and 8B depict a medication cartridge 102 as being installed or otherwise inserted into the cartridge carrier 200. As shown, the alignment features 406 (i.e., opposing protrusions) provided a keyed connection and alignment by passing through the channels 408 and slots 606 to allow the cartridge 102 to be contained within the carrier 200. As shown in FIG. 9, the alignment feature 406 has travelled through the first slot 708 and channel 408 to rest at the first junction 714. In this position, the medication cartridge 102 is held within the dispensing device in a stored position. Since the alignment feature 406 is at a fixed location within the cartridge carrier 200, and because the second slot 710 and channel 408 descend downwards at an angle from the first junction 714, rotation of the cartridge carrier 200 necessarily forces the medication cartridge 102 upwards within the cartridge carrier 200. These aspects are further depicted in FIGS. 10A through 10C.

Figures 10A, 10B, 10C:
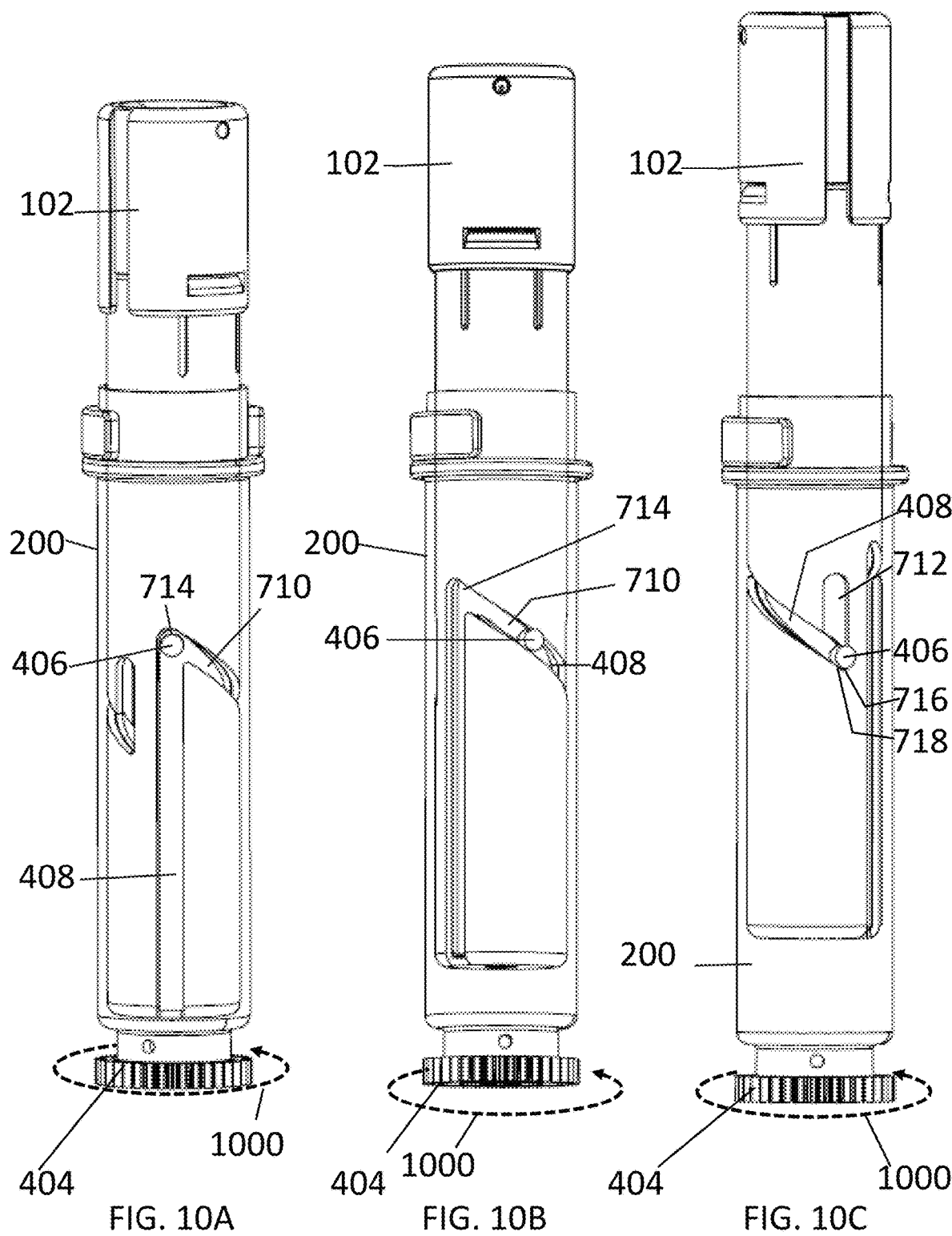
FIG. 10A shows an exemplary illustration of the medication cartridge inserted into the cartridge carrier, depicting the medication cartridge in a stored position.
FIG. 10B shows an exemplary illustration of the medication cartridge inserted into the cartridge carrier, depicting the cartridge carrier rotating to move the medication cartridge up and toward the dispensing position.
FIG. 10C shows an exemplary illustration of the medication cartridge inserted into the cartridge carrier, depicting the cartridge carrier as rotated to move the medication cartridge up and into the dispensing position.

FIG. 10A depicts the medication cartridge in a stored position. As shown, the alignment feature 416 rests within the first junction 714. As shown in FIG. 10B, rotation 1000 (via the gear wheel 404) of the cartridge carrier 200 forces the alignment feature 416 to traverse through the second slot 710 and channel 408 away from the first junction 714. In doing so and as shown, the medication cartridge 102 is lifted upwards within the cartridge carrier 200. Further rotation 1000 of the cartridge carrier 200, as shown in FIG. 10C, results in the alignment feature 416 to traverse until it rests within the second junction 716 and the channel 408 terminates at the channel terminal 718. Notably, when the alignment feature 416 is at the second junction 716, the medication cartridge 102 is lifted from the dispensing device 100 into the dispensing position. Thus, the journey of the protrusions commences from the first junction 714, progressing towards the second junction 716. As a consequence of this carefully guided pathway, the medication cartridge 102 experiences an upward shift. This movement is instrumental in the transition of the medication cartridge 102 from what is denoted as the 'stored position' to its final location, the 'dispensing position'.

While the cartridge 102 is in the dispensing position, the vial 602 therein is in the expanded state and ready to be compressed to dispense medication. As shown in FIGS. 11A through 11C, although the channel 408 in the vial 602 has terminated, the slot in the shell 600 continues upwards as the third slot 712. Thus, when the medication cartridge 102 is in the dispensing position, a user can selectively press down on the medication cartridge 102 to cause the vial 602 to slide within the shell 600. As shown in FIG. 11C, due to the stepped inner wall 1100 and end of the channel 408, the vial 602 is held in place by the alignment features 406 and only the outer shell 600 can travel downward when pressed down, causing the shell 600 to slide downward over the vial 602 and allowing the pump assembly to be actuated and spray/dispense the medication. This feature is further illustrated in FIGS. 12A and 12B. As shown, pressing downward 1200 on the medication cartridge 102 causes the alignment features 406 to travel upwards through the third slot 712, thereby forcing the shell 600 downward while holding the vial 602 in place. While the shell 600 is forced downward, it compresses the vial 602 from the expanded to compressed state. The transition from the expanded to compressed state activates the pump assembly to force medication 1202 from the vial 602 and through the dispensing aperture 604, similar to a squirt of medication. The pump assembly can be configured as a spring-loaded pump mechanism that lifts the shell 600 after being compressed, thereby returning the alignment features 406 to the second junction 716. Once dispensed, the dispensing device 100 and associated activator mechanism 300 can be activated to turn the gear wheel 404 in an opposite direction as previously rotated. Such a rotation lowers the medication cartridge 102 back to the stored position as the alignment features 406 are forced back to the first junction 714 (shown in FIG. 10A).

In one aspect, the device 100 is formed to sense once a predetermined number of squirts (e.g., one, etc., as prescribed) have been initiated so that it automatically activates the activator mechanism 300 to return the medication cartridge 102 back to the stored position, thereby retracting the medication cartridge 102 and inaccessibility after user. For example, magnetic sensors, a trigger, electrical sensors, light sensors, or any other means for determining if medication has been dispensed from the vial 602 can be included within the device 100. As a non-limiting example, a magnet can be positioned at the bottom of the shell 600 while a magnetic reed switch is similarly positioned at the bottom of the cartridge carrier 200. Pressing the medication cartridge 102 and its shell 600 downward within the cartridge carrier 200 brings the magnet into close proximity of the magnetic reed switch to notify the associated electronics (integrated circuit, etc.) that a single squirt has been dispensed. After the predetermined number of squirts, the activator mechanism is activated to rotate the cartridge carrier 200 and return the medication cartridge 102 to the stored position to prevent further and unauthorized use. In another aspect, the device 100 can be include any necessary components (integrated circuit, etc.) to allow for a timed configuration in which the medication cartridge 102 is held in the dispensing position. For example, the device 100 can be programmed such that after authentication and movement of the medication cartridge 102 into the dispensing position, it is returned to the stored position after a predetermined or preprogrammed amount of time (e.g. 2 seconds, etc.).

As noted above, a unique design feature allows for the vial 602 to exist in two distinct states; namely an expanded state and a compressed state. The transition between these two stages is critical to the functionality of the device. When it moves from the expanded state towards the compressed state, the incorporated pump assembly 700 is triggered into action. This incorporation of a pump assembly 700 and its associated operation indicates an upbeat sophistication of the one embodiment, going beyond traditional static medical dispensing devices. The purpose of this actuation is specifically to ensure the controlled release of the medicine within the vial 602. On the actuation of the pump assembly 700, the medicine 1202 is pushed out of the vial's 602 outlet. This outflow proceeds under the controlling and moderating role of the pump assembly 700, guaranteeing a controlled and managed release of the medicine.

Thus and as noted above, present disclosure provides an innovative medication dispensing device 100 that can be interfaced with and/or controlled by an external device. The core of this medication dispensing device 100 revolves around a unique cartridge carrier 200 design, integrated with a pair of opposing protrusions 406 and a uniquely designed medication cartridge that is functionally designed to operate based on the positioning of the protrusions 406 after user authentication. As noted above, in one aspect, the device 100 includes a authentication component 106. Upon successful authentication, the authentication component 106 triggers the activator mechanism 300. In this context, the activation entails the initiation of moving the medication cartridge 102. When activated, it can efficaciously induce the cartridge carrier 200 mechanism to actuate, progressing the inserted medication cartridge 102 from a stored position to a dispensing position. Maximal effectiveness is ensured as the activator mechanism 300 is engendered only after a successful user authentication process, thereby verifying that the medication is dispensed to the appropriate user. This sequence not only ensures secure and controlled dispensing of the medication but also minimizes errors and the potential for unlawful access. In one aspect, the interconnectedness between the authentication component 106 and the activator mechanism 300 forms the crux of this dispensing device 100, thereby augmenting the overall safety and operation of the dispensing device 100. Moreover, this intricate mechanism, in coordination with the user and the cartridge carrier 200, ensures that the process of moving the medication cartridge 102 from a stored position to a dispensing position is not only smooth but also efficient and secure.

Thus, in one aspect, a purpose of this inventive operation is to modify the positioning of the medication cartridge 102 from a state of storage to a dispensing state, thereby facilitating the delivery of medication in a controlled, efficient, and timely manner. The operational process involved in use of the dispensing device 100 advances through several stages, starting with the activation of the activator mechanism 300. The initiation of this mechanism 300 leads to a rotational motion in the cartridge carrier 200, a critical movement that fosters the maneuvering of the pair of opposing protrusions 406 (i.e., alignment features). This rotation is precisely designed to stimulate this movement, making the entire process efficient and seamless. The pair of opposing protrusions 406 are guided in their motion by a pair of opposing slots 606 in conjunction with a pair of opposing channels 408. These channels 408 and slots 606 function in harmony, not only providing a safe passage but also controlling the direction of the movement of these protrusions 406 while guiding the medication cartridge 102 between a stored position and a raised dispensing position. The unique features of the slots 606 and channels 408 also allow a user to compress the vial 602 within the medication cartridge 102 to dispense medication 1202.

(2.2) System, Method, and Computer Program Product

Figure 13:
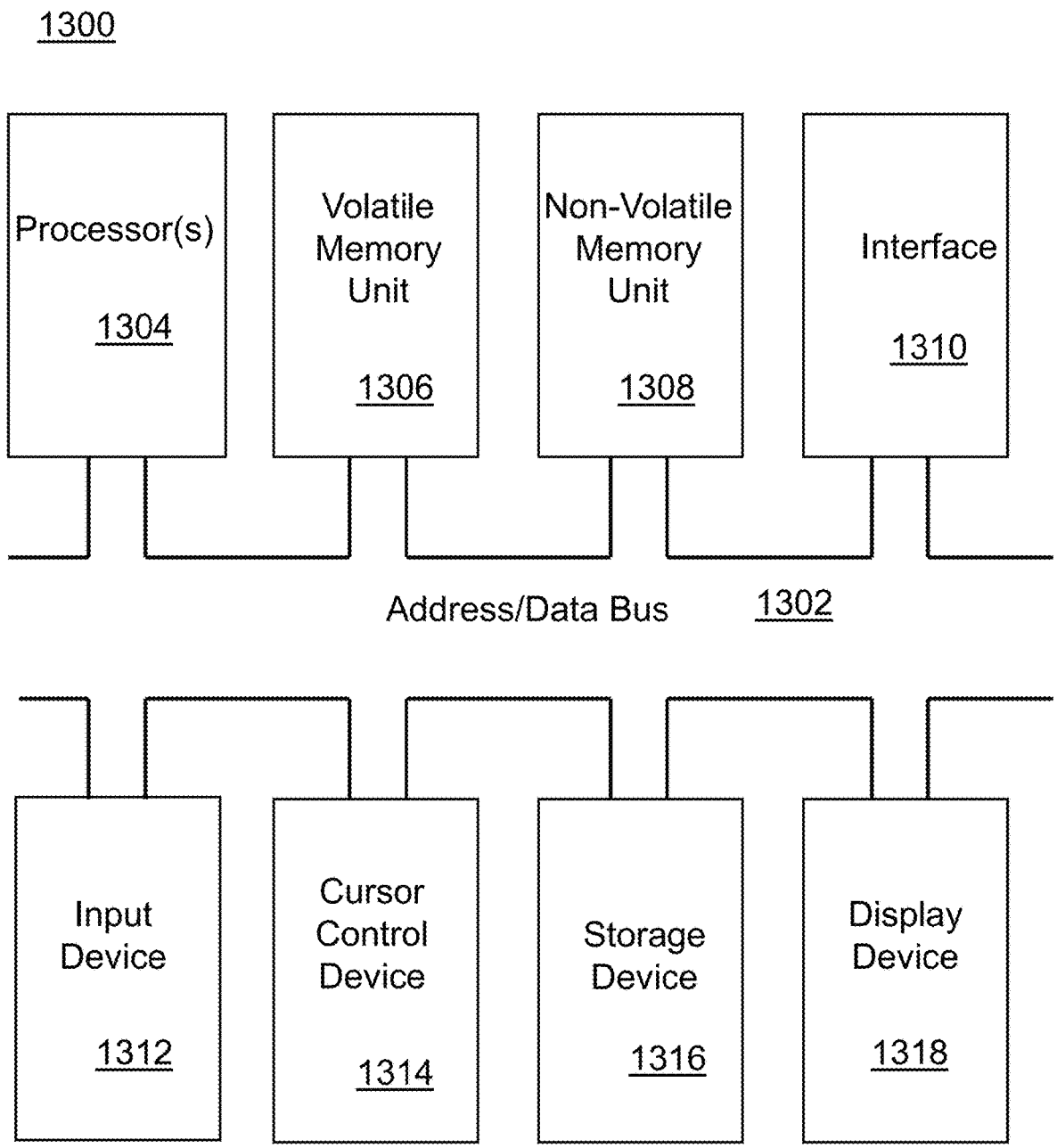
FIG. 13 is a block diagram depicting the components of a system according to various embodiments of the present invention.

As noted above, the present disclosure provides both a patient system (and method and computer program product) and caregiver system (and method and computer program product) for interfacing with and/or controlling a medication dispensing device. Both systems are implemented on any suitable external device (e.g., mobile phone (wireless device), tablet computer, desktop computer, etc.) that includes the programing and any other necessary information and/or components to allow for interfacing with and/or controlling the medication dispensing device and/or communicating with one another. A block diagram depicting an example of a computer system 1300 that can be utilized for either of the patient system and caregiver system is provided in FIG. 13. The computer system 1300 is configured to perform calculations, processes, operations, and/or functions associated with a program or algorithm and communicate with the medication dispensing device using any suitable communication technique (e.g., via the internet, WiFi, Bluetooth, etc.). In one aspect, certain processes and steps discussed herein are realized as a series of instructions (e.g., software program) that reside within computer readable memory units and are executed by one or more processors of the computer system 1300. When executed, the instructions cause the computer system 1300 to perform specific actions and exhibit specific behavior, such as described herein. In various aspects, the computer system 1300 can be embodied in any device(s) that operates to perform the functions as described herein as applicable to interfacing with and/or controlling the medication dispensing device, such as a desktop computer, a mobile or smart phone, a tablet computer, a computer embodied in a mobile platform, or any other device or devices that can individually and/or collectively execute the instructions to perform the related operations/processes. Thus, it should be understood that the example as depicted in FIG. 13 is a non-limiting example of one embodiment and that the invention is not intended to be limited thereto. For example, the computer system 1300 in one aspect is desirably incorporated into a wireless external device, such as a mobile phone or tablet computer, or a remote server (networked to the internet), or any combination thereof as designed and/or desired.

The computer system 1300 may include an address/data bus 1302 (or any other components as necessary) that is configured to communicate information. Additionally, one or more data processing units, such as a processor 1304 (or processors), are coupled with the address/data bus 1302. The processor 1304 is configured to process information and instructions. In an aspect, the processor 1304 is a microprocessor. Alternatively, the processor 1304 may be a different type of processor such as a parallel processor, application-specific integrated circuit (ASIC), programmable logic array (PLA), complex programmable logic device (CPLD), or a field programmable gate array (FPGA) or any other processing component operable for performing the relevant operations.

The computer system 1300 is configured to utilize one or more data storage units. The computer system 1300 may include a volatile memory unit 1306 (e.g., random access memory ("RAM"), static RAM, dynamic RAM, etc.) coupled with the address/data bus 1302, wherein a volatile memory unit 1306 is configured to store information and instructions for the processor 1304. The computer system 1300 further may include a non-volatile memory unit 1308 (e.g., read-only memory ("ROM"), programmable ROM ("PROM"), erasable programmable ROM ("EPROM"), electrically erasable programmable ROM "EEPROM"), flash memory, etc.) coupled with the address/data bus 1302, wherein the non-volatile memory unit 1308 is configured to store static information and instructions for the processor 1304. Alternatively, the computer system 1300 may execute instructions retrieved from an online data storage unit such as in "Cloud" computing. In an aspect, the computer system 1300 also may include one or more interfaces, such as an interface 1310, coupled with the address/data bus 1302. The one or more interfaces are configured to enable the computer system 1300 to interface with other electronic devices and computer systems. The communication interfaces implemented by the one or more interfaces may include wireline (e.g., serial cables, modems, network adaptors, etc.) and/or wireless (e.g., wireless modems, Bluetooth, WiFi, wireless network adaptors, etc.) communication technology. Further, one or more processors 1304 (or devices) can be associated with one or more associated memories, where each associated memory is a non-transitory computer-readable medium with instructions encoded thereon. Each associated memory can be associated with a single processor 1304 (or device), or a network of interacting processors 104 (or devices).

In one aspect, the computer system 1300 may include an input device 1312 (e.g., coupled with the address/data bus 1302 and/or a user interface), wherein the input device 1312 is configured to communicate information and command selections to the processor 1304. In accordance with one aspect, the input device 1312 is an alphanumeric input device, such as a keyboard, that may include alphanumeric and/or function keys. Alternatively, the input device 1312 may be an input device other than an alphanumeric input device. In an aspect, the computer system 1300 may include a cursor control device 1314 coupled with the address/data bus 1302, wherein the cursor control device 114 is configured to communicate user input information and/or command selections to the processor 1304. In an aspect, the cursor control device 1314 is implemented using a device such as a mouse, a track-ball, a track-pad, an optical tracking device, or a touch screen. The foregoing notwithstanding, in an aspect, the cursor control device 1314 is directed and/or activated via input from the input device 1312, such as in response to the use of special keys and key sequence commands associated with the input device 1312. In an alternative aspect, the cursor control device 1314 is configured to be directed or guided by voice commands.

In an aspect, the computer system 1300 further may include one or more optional computer usable data storage devices, such as a storage device 1316, coupled with the address/data bus 1302. The storage device 1316 is configured to store information and/or computer executable instructions. In one aspect, the storage device 1316 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 1318 is coupled with the address/data bus 1302, wherein the display device 1318 is configured to display video and/or graphics. In an aspect, the display device 1318 may include a liquid crystal display ("LCD"), field emission display ("FED"), plasma display, or any other display device suitable for displaying video and/or graphic images and alphanumeric characters recognizable to a user.

In an aspect and as noted above, the system 1300 may be implemented as an external wireless device, such as a mobile phone or tablet computer, where the input device 1302 is integrated into the display device 1318. Thus, in this aspect, the input device 1302 is the screen on the wireless device, allowing user to visually see the user interface and input selections, information, and commands. Further, if the patient system and/or caregiver system (each of which are computer systems 1300) are designed to use a remote server for any of the functions described herein, the remote server is yet another networked computer system 1300 in accordance with embodiments of the present disclosure and considered to be an integral part of each of the patient system and caregiver system for storage and other functions as desired.

The computer system 1300 presented herein is an example computing environment in accordance with an aspect. However, the non-limiting example of the computer system 1300 is not strictly limited to being a computer system. For example, an aspect provides that the computer system 1300 represents a type of data processing analysis that may be used in accordance with various aspects described herein. Moreover, other computing systems may also be implemented for either of the patient system or caregiver system (and the remote server), or any combination thereof. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 14:
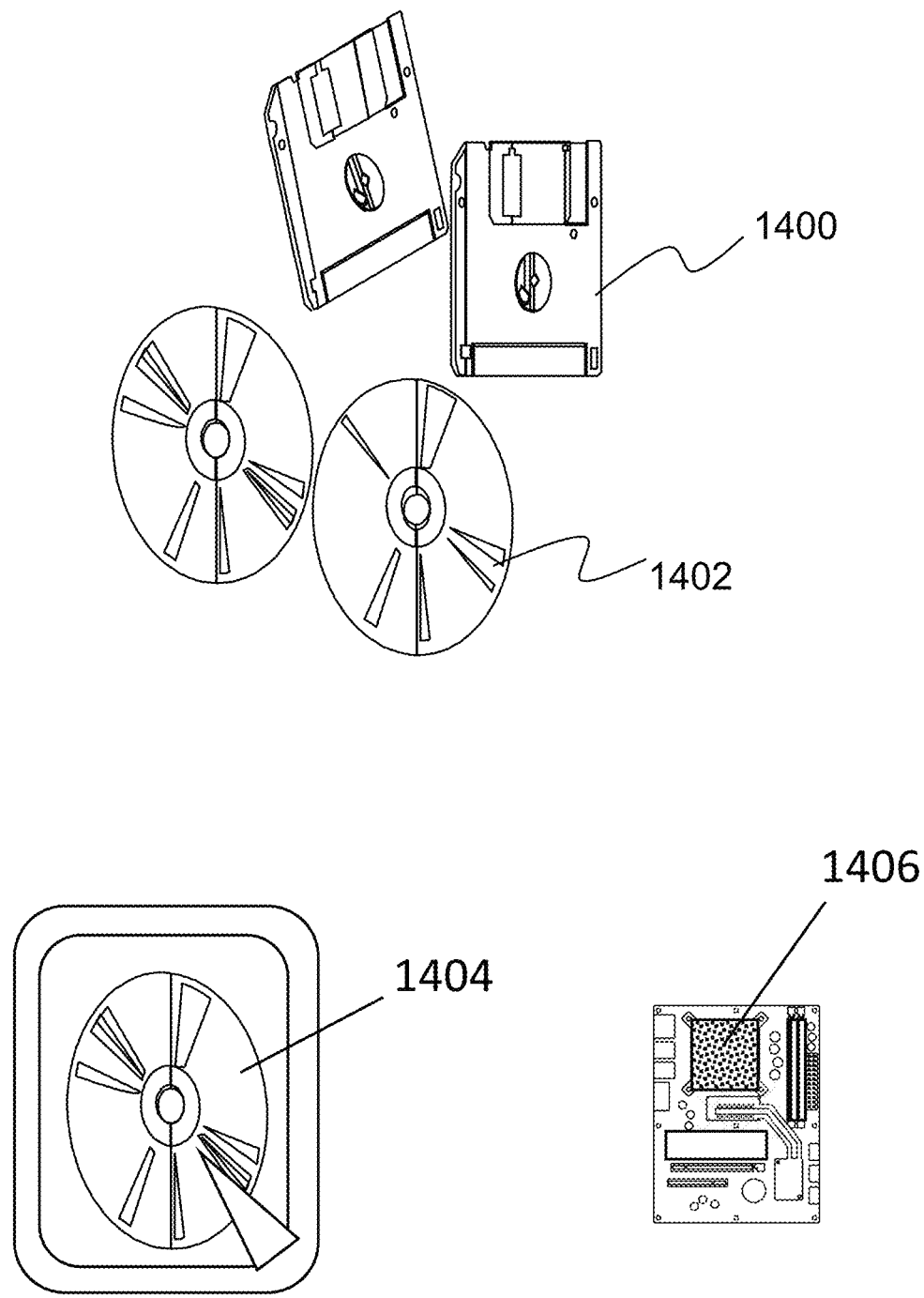
FIG. 14 is an illustration of a computer program product embodying an aspect of the present invention.

An illustrative diagram of a computer program product (i.e., storage device) embodying the software application (for either of the patient and/or caregiver systems) of present invention is depicted in FIG. 14. The computer program product is any computer readable medium having executable (computer-readable) instructions stored thereon. As a non-limiting example, the computer program product is depicted as floppy disk 1400, an optical disk 1402 such as a CD or DVD, a hard drive 1404, or a digital non-volatile flash memory 1406 (e.g., flash chips as used on phones and tablets and as soldered into the board). However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, a flash drive, or flash chip. In either event, the instructions are encoded on a non-transitory computer-readable medium and are configured to cause the associated processor and system to perform the encoded operations.

Several non-limiting examples of operations as provided for by the instructions and present disclosure are depicted in FIGS. 15 through 20D. For instance, the present disclosure provides a Patient System 1500 that can be operated by a patient to provide a variety of operations/data/etc. and that can be accessed by the patient using said system. The patient system 1500 operates as a computer system that can operate as a stand-alone computer system or, in other aspects, be networked to include other computer systems (e.g., the remove server 1504, etc.) that house coded instructions and memory as needed to provide the functions as described herein. For example, in some aspects, the user's mobile phone (i.e., an external computing device) has a software app which operates as an interface for the patient system 1500 with the database regarding patient specifics stored on the remote server 1504; thus, the patient system 1500 includes both the user's external computing device as well as the remote server 1504. A flowchart depicting the architecture/process flow of the patient system is depicted in FIGS. 16A through 16E. As shown in FIG. 16A, upon loading the patient system (e.g., opening the patient app on a user's mobile phone), the patient system provides (via a display, such as the mobile phone screen) a splash screen in which a user can select if they are a patient or caregiver and login or register accordingly. After logging in or registering as a patient, the system provides the option to set up the medication dispensing device. The medication dispensing device is then registered to the particular user through a unique identifier that can be added using any suitable technique. As a non-limiting example, such an identifier can be manually added, entered through scanning a bar code or QR code (with the camera on the system (i.e., where the system is incorporated into an external device such as the user's mobile phone), pairing through Bluetooth, etc. It should also be noted that each medication cartridge can be associated and/or registered to each user or the specific medication dispensing device in a similar manner, where the medication cartridge has a unique identifier that is either entered into the system (using similar techniques are referenced above regarding the dispensing device), or recognized directly by the medication dispensing device using any suitable technique (such as RFID described above).

Figure 16A:
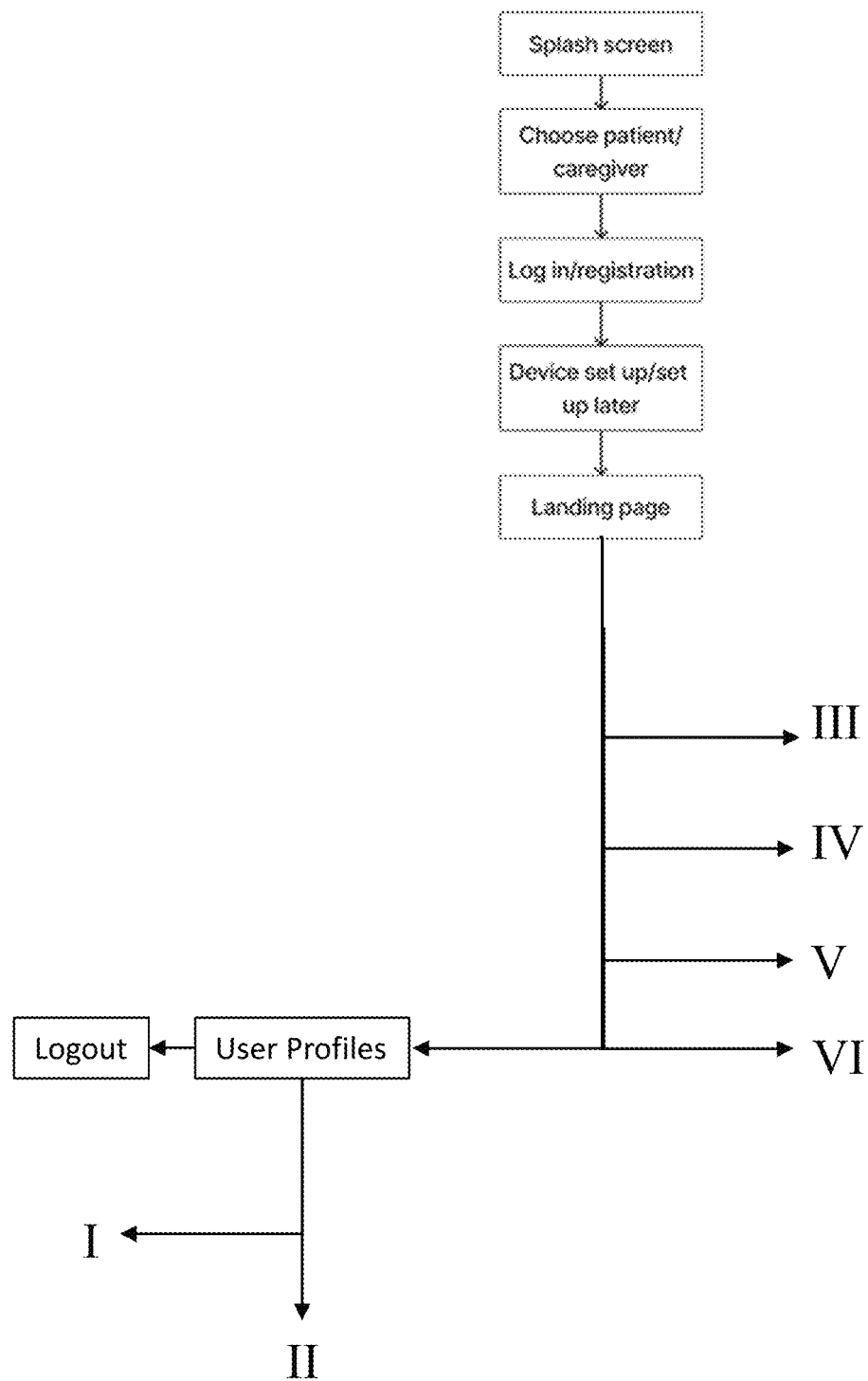
FIG. 16A is an illustration depicting a process flow of a patient system architecture according to various embodiments of the present invention.
Figure 16B:
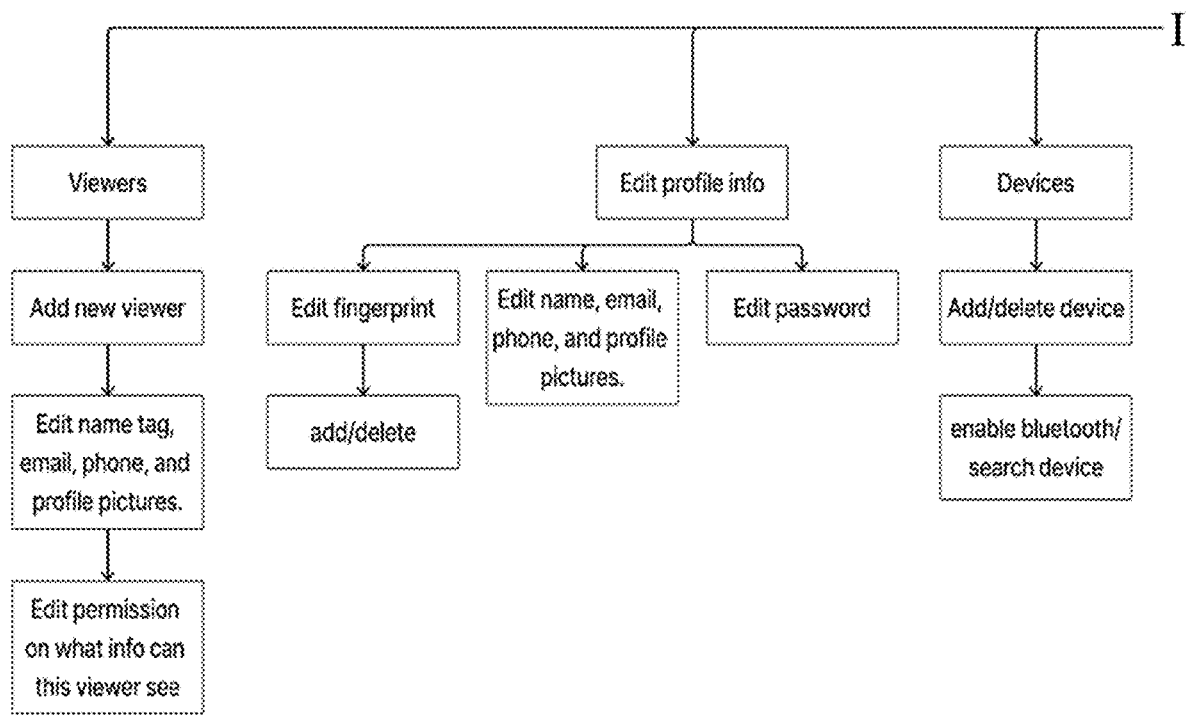
FIG. 16B is an illustration depicting the process flow of the patient system architecture flowing from FIG. 16A.
Figure 16C:
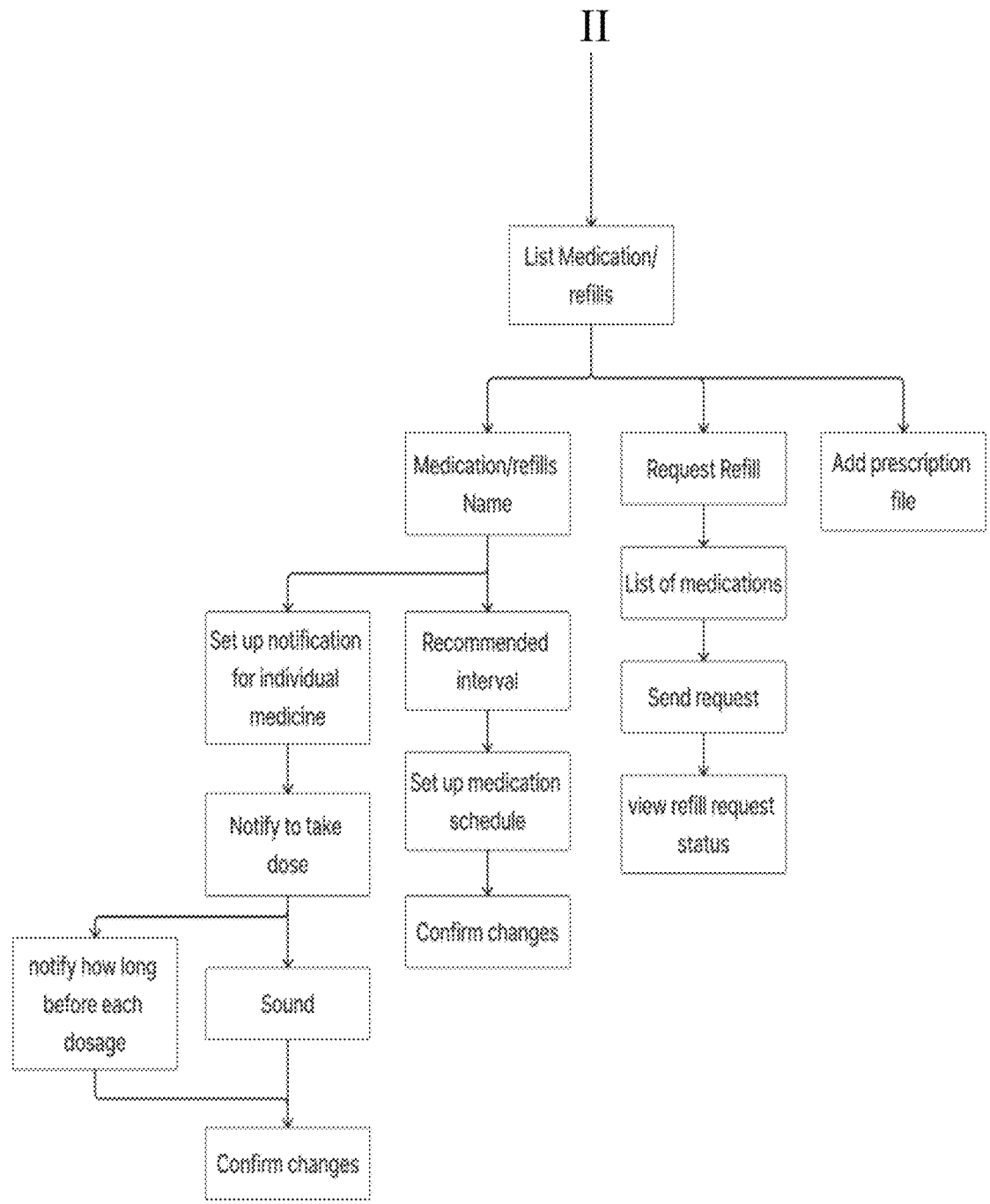
FIG. 16C is an illustration depicting the process flow of the patient system architecture flowing from FIG. 16A.
Figure 16D:
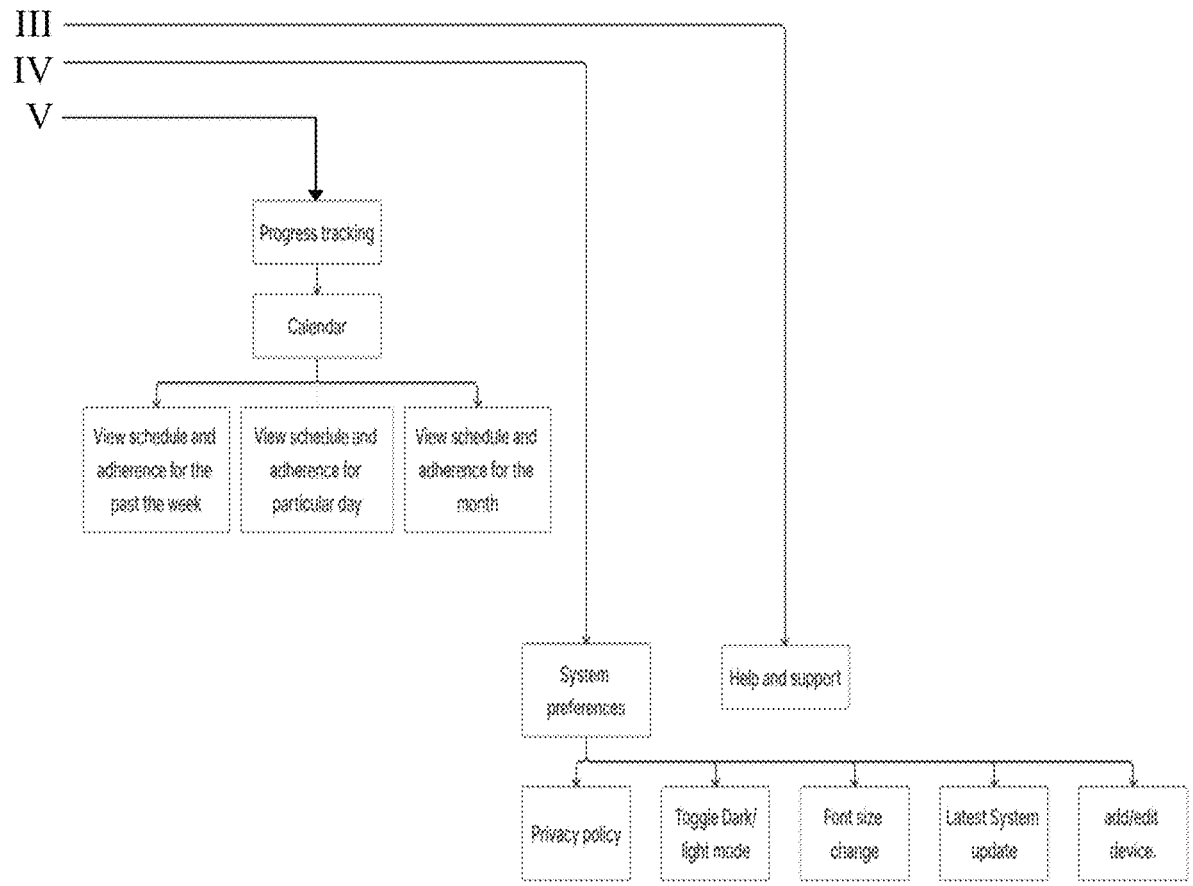
FIG. 16D is an illustration depicting the process flow of the patient system architecture flowing from FIG. 16A.
Figure 16E:
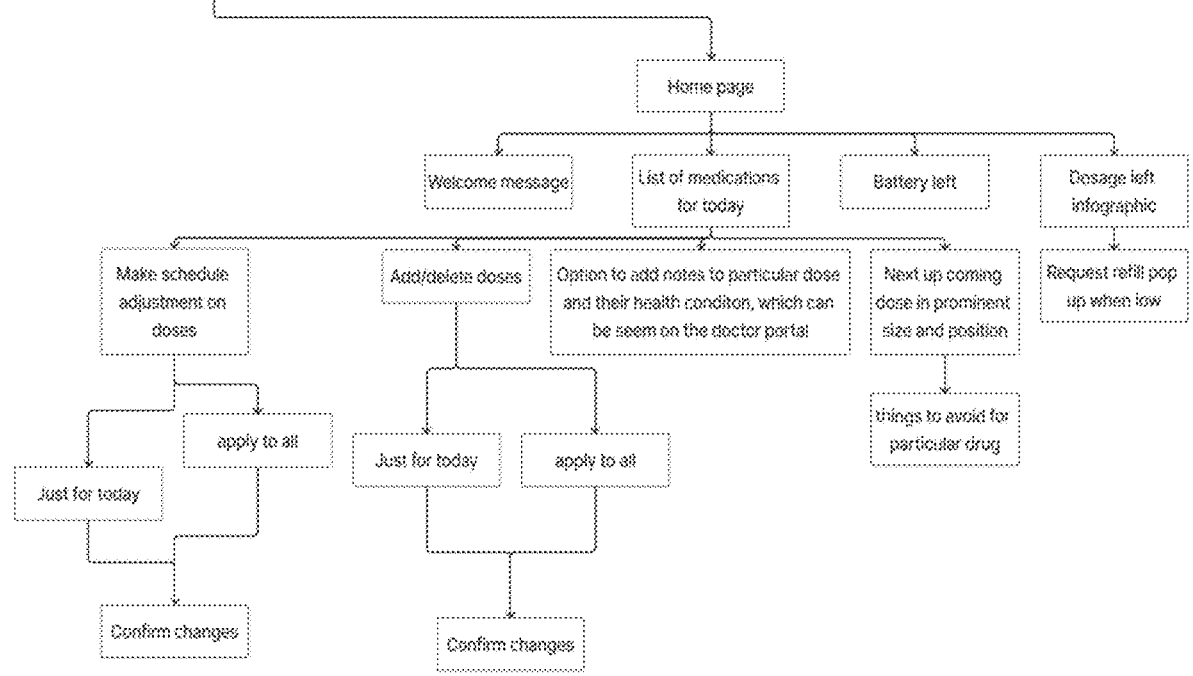
FIG. 16E is an illustration depicting the process flow of the patient system architecture flowing from FIG. 16A.

As shown throughout the flowcharts in FIGS. 16A through 16E, after addressing the device setup, the user is provided a landing page with several features and options, including a home phone (as shown in FIG. 16E), a user profile page (as shown in FIG. 16A and subsequently FIGS. 16B and 16C), and a progress tracking page and system preferences page (as shown in FIG. 16D).

In one aspect and as shown in FIG. 16E, the home page can be used to display and manage a variety of features regarding a particular patient's prescription. Several non-limiting examples of features include showing lists of medications that needed to be taken on a current day, displaying (via an infographic) doses currently available in the medication dispensing device, infographics to display necessary doses left for each medication at any moment in time, etc. In one aspect, when the system is linked to the medication dispensing device, the system is notified of dosage usage by the dispensing device to calculate remaining doses left. In other aspects, the dispensing device communicates usage through any suitable transmission technique, including WiFi, Bluetooth, etc. Doses are automatically updated when taken through the dispensing device. Further, in some aspects, users have options to add/delete doses manually, while there is also a prominent display (via the display screen of the system) of the next upcoming dose.

As shown in FIGS. 16A through 16C, the user profile page provides several features of managing a user profile. For example, the system can be configured to allows users to access their list of medications and order refills, to add/delete/edit devices, an option to edit profile information, as well as the option to add/delete/edit viewers of their medication data through the app (e.g., there is a viewer mode in the app to view other user data if approved to do so). In one aspect, the system stores the user biometric data (e.g., fingerprint) to allow for authentication and access to the device. As shown in FIG. 16B, the user profile section allows a user to edit the fingerprint (or facial recognition, etc.) on file for the authorized user of the device. For example and as shown in FIG. 15, if selecting to add a fingerprint and when the patient system 1500 is paired to the medication dispensing device 100, the user can place a fingerprint on the authentication component 106 (e.g., fingerprint reader) to scan/read a new fingerprint that is to be stored (e.g., stored in the patient system 1500 (external device (users mobile phone) and/or remote server) and/or in the integrated circuit/memory of the dispensing device 100 itself) as an authenticated user of the medication dispensing device 100. For example, upon authentication by the patient system 1500, the dispensing device is allowed to operate and activate the activator mechanism, thereby causing the dispensing device to be activated only upon authentication by the patient system 1500. As understood by those skilled in the art, several other operable features are also depicted in the flowcharts.

As shown in FIG. 16D, the patient system can also be configured to provide a progress tracking page as well as a system preferences page, and associated features/operations. As a non-limiting example, the progress tracking page: (1) displays a calendar with days that are selectable and shows adherence data for the user's medications on that day, (2) allows users to view and edit their doses scheduled for current and future dates, and (3) also allows viewers to view this data through infographics that are displayed by day, week, and month. Further, in one aspect, the system preferences page: (1) allows users access to app specific settings, such as light/dark mode, font size, and system updates, (2) allows users to add/edit a device to the app/their account, and (3) lets users see privacy policy forms again after they viewed it in their initial sign-up sequence.

In one aspect and as shown in FIG. 15, the patient system 1500 can be accessed and interacted with (via the Internet, WiFi, Bluetooth, etc.) by a separate caregiver system 1502 and/or doctor portal. Caregivers are parties that are allowed by the patient to view the patient's particular medication or treatments, non-limiting examples of which include family members, nurse assistants, nurses, etc. (collectively referred to herein as "caregivers"). Thus, while the computer system 1300 above is described with respect to a patient system, all of the relevant hardware and software is equally applicable to a separate caregiver system, method, and computer program product. In other words, the caregiver system includes all necessary components to operate and provide the operations as described herein, non-limiting examples of which include the features, items, and components as described with respect to FIGS. 13 and 14. Desirably, the caregiver system 1502 as shown in FIG. 15 is incorporated into an external device such as a mobile phone or tablet computer (although it can be implemented on a desktop or any other suitable computer system) and can include and/or operate any other connected or networked devices as needed to facilitate the functions or operations as described here, including an optional remote server 1504 that can be included in some aspects if desired to store user data, source code, etc. as can be understood by those skilled in the art. The remote server 1504 (in conjunction with a doctor portal device (i.e., mobile phone, tablet computer, laptop, desktop computer, etc.)) can also optionally serve as a doctor portal system 1506 in which a doctor can view and store patient information and modify prescriptions, etc. that are stored in the remote server and pushed (transmitted) through to the patient system 1500 and/or caregiver system 1502. Thus, the doctor can generate modified does schedules that are pushed (transmitted) through to the patient system 1500 and/or caregiver system 1502, with the dispensing device being operable if within the parameters of the modified dose schedule.

In other aspects, the caregiver system 1502 can be modified with doctor specific information such that the caregiver system 1502 itself operates as the doctor portal system. In this aspect, such a caregiver system 1502 would be responsible for creating patient profiles and generating the invitation link referenced further below, as well as other doctor specific features (such as modifying authorized dose schedules (e.g., amount per time of medication to be dispensed) that are pushed (transmitted) to the patient system 1500, etc.).

Notably, the caregiver system 1502 is configured as a viewer platform or app that can interface with the patient system 1500 and/or dispensing device 100, and that allows users to view the data and adherence of people who have approved them to do so (family members, caregivers, etc.). A flowchart depicting the architecture/process flow of the caregiver system is depicted in FIGS. 17A through 17D.

Figure 17A:
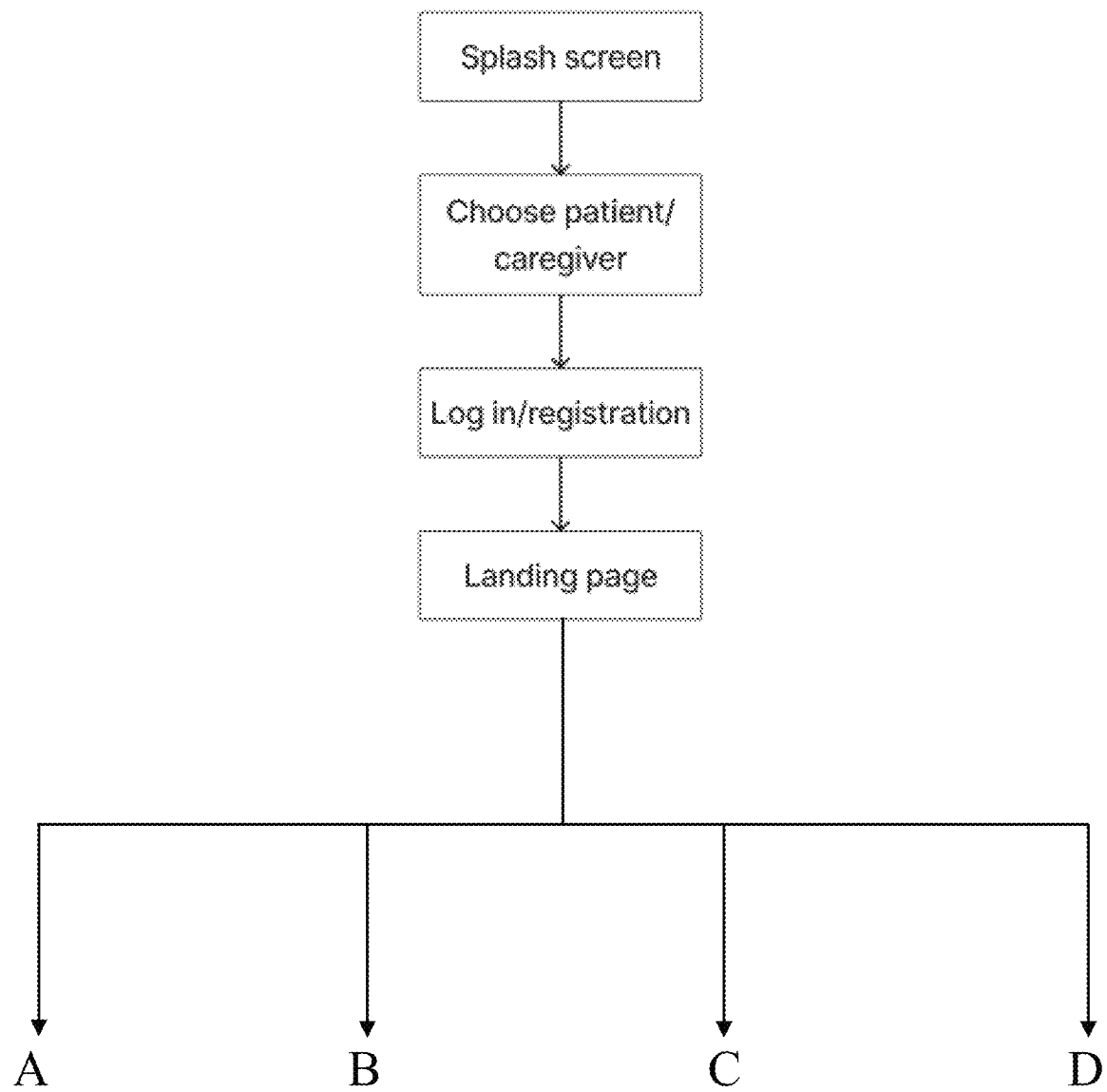
FIG. 17A is an illustration depicting a process flow of a caregiver system architecture according to various embodiments of the present invention.

As shown in FIG. 17A, upon loading the caregiver system (e.g., opening the app on a user's mobile phone), the system provides (via a display, such as the mobile phone screen) a splash screen in which a user can select if they are a patient or caregiver and login or register accordingly. After logging in or registering as a caregiver, the caregiver system provides a landing page with any suitable caregiver feature. For example, the landing page can include several options, such as links to a user profile page (shown in FIG. 17B), a home page (shown in FIG. 17C), and a systems preferences page (shown in FIG. 17D).

The home page is configured to provide any suitable functionality to operate as a caregiver portal. As a non-limiting example and as shown in FIG. 17C, the home page allows the user/caregiver to see a list of patents who they are permitted to view. For example, once the user selects a particular patient, it will show that patient's list of medications for the day. Depending on the permissions of the user they may be able to: (1) make dose schedule adjustments for a patient, (2) add/delete doses for a patient, and (3) add notes regarding patient condition. Caregivers may also add/delete/edit patients to their list that they can view and/or interface with.

In one aspect, the caregiver could make dose schedule adjustments for the patient with are then updated on the patient side via their patient system. Further and in one aspect, when the patient interfaces with the medication dispensing device, the medication dispensing device will only be operable and allow for activation of the activator mechanism if the attempted operation is within the dose schedule. Thus, in this example, the caregiver system pushes (transmits) dose schedule adjustments through to the patient system and/or dispensing device, thereby causing the dispensing device to be activated only upon authorization of the caregiver system.

Figure 17B:
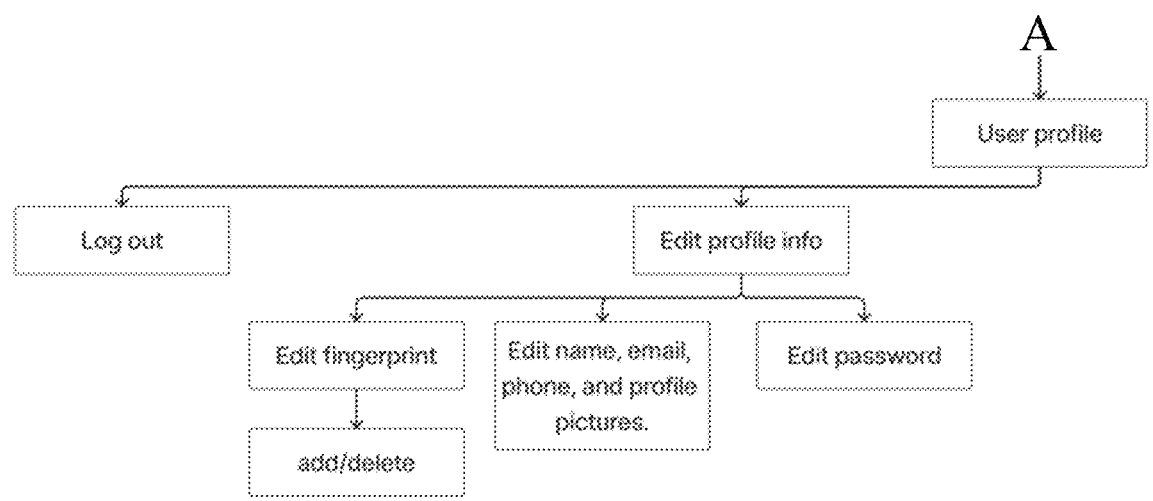
FIG. 17B is an illustration depicting the process flow of the caregiver system architecture flowing from FIG. 17A.
Figure 17C:
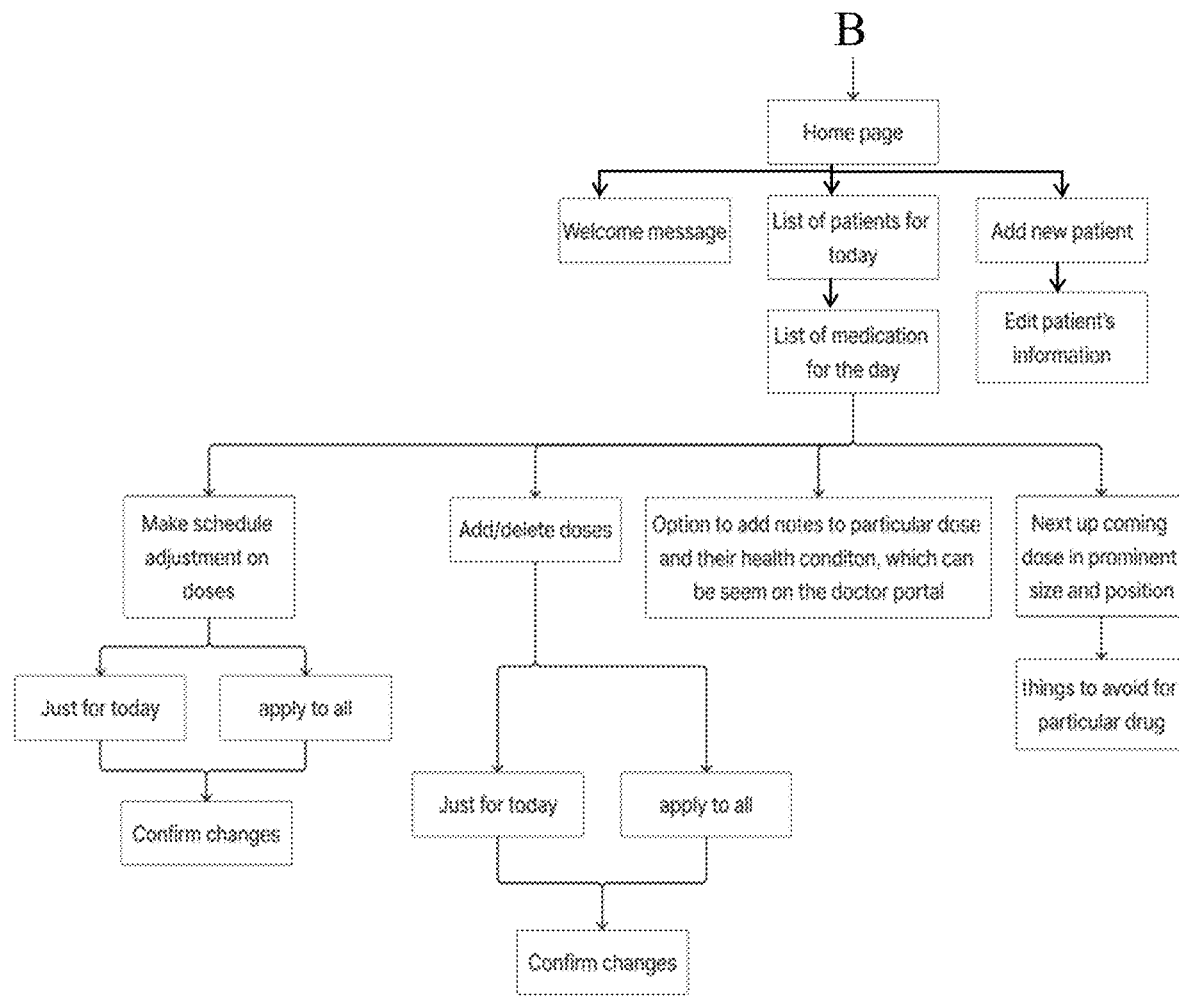
FIG. 17C is an illustration depicting the process flow of the caregiver system architecture flowing from FIG. 17A.

As was the case above with the patient system, the caregiver system also includes a user profile page (flowchart depicted in FIG. 17B). The user profile page, for example, allows the viewer/caregiver to edit their own personal profile info (name, email, password, etc.). In some aspects, the viewer/caregiver can also add/delete/edit biometric data (e.g., fingerprints) that can be used on the medication dispensing devices of patients they are viewing (if, for example, the patient grants them access to).

Figure 17D:
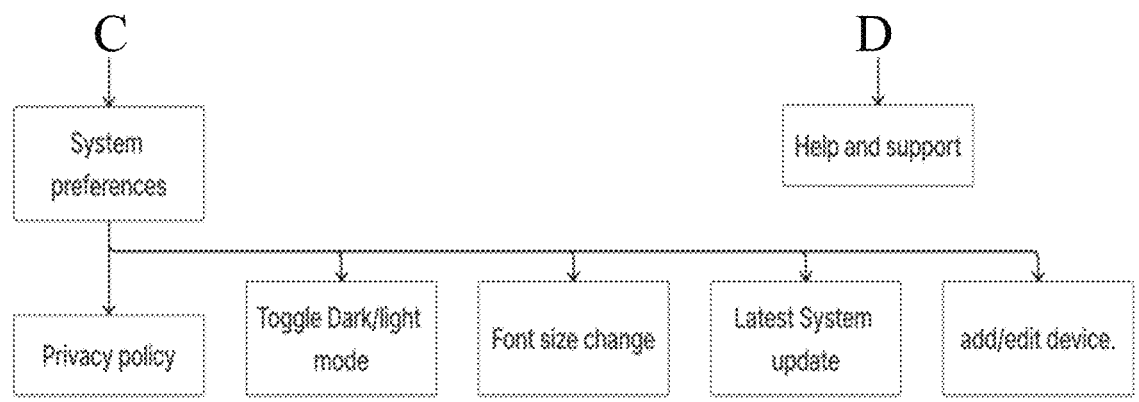
FIG. 17D is an illustration depicting the process flow of the caregiver system architecture flowing from FIG. 17A.

As shown in FIG. 17D, the caregiver system also includes a system preferences page and related operations, including operations that: (1) allows users access to app specific settings, such as light/dark mode, font size, and system updates, (2) allows users to add/edit a device to the app/their account, and (3) lets users see privacy policy forms again after they viewed it in their initial sign-up sequence.

As noted above, the caregiver system includes one or more computer systems (e.g., external wireless device such as a mobile phone and/or remote server, etc., or any combination thereof) and any other components, software, etc. as may be necessary and/or desired to facilitate the operations as described herein. Similarly and also as noted above, patient system includes one or more computer systems (e.g., external wireless device and/or remote server, etc., or any combination thereof) and any other components, software, etc. as may be necessary and/or desired to facilitate the operations as described herein.

As can be appreciated by those skilled in the art, the patient system and caregiver system collectively provide a unique system that can help to facilitate medication dispensing in a controlled and safe manner to eliminate errors and increase ease of use. Several non-limiting examples of use scenarios are depicted in the process flow charts as referenced below.

Figure 18A:
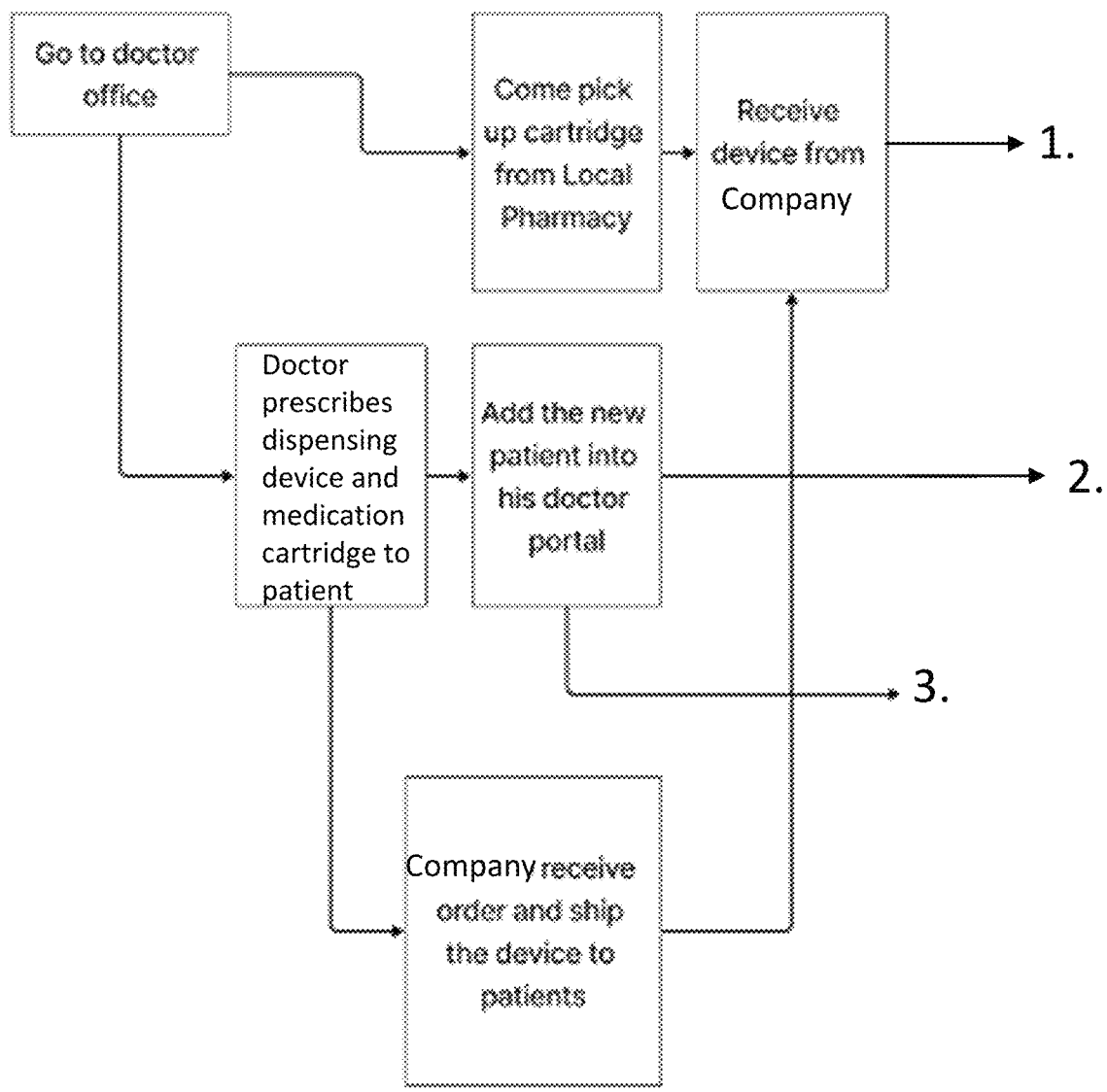
FIG. 18A is an illustration depicting a process flow for an example patient scenario and operation according to various embodiments of the present invention.
Figure 18B:
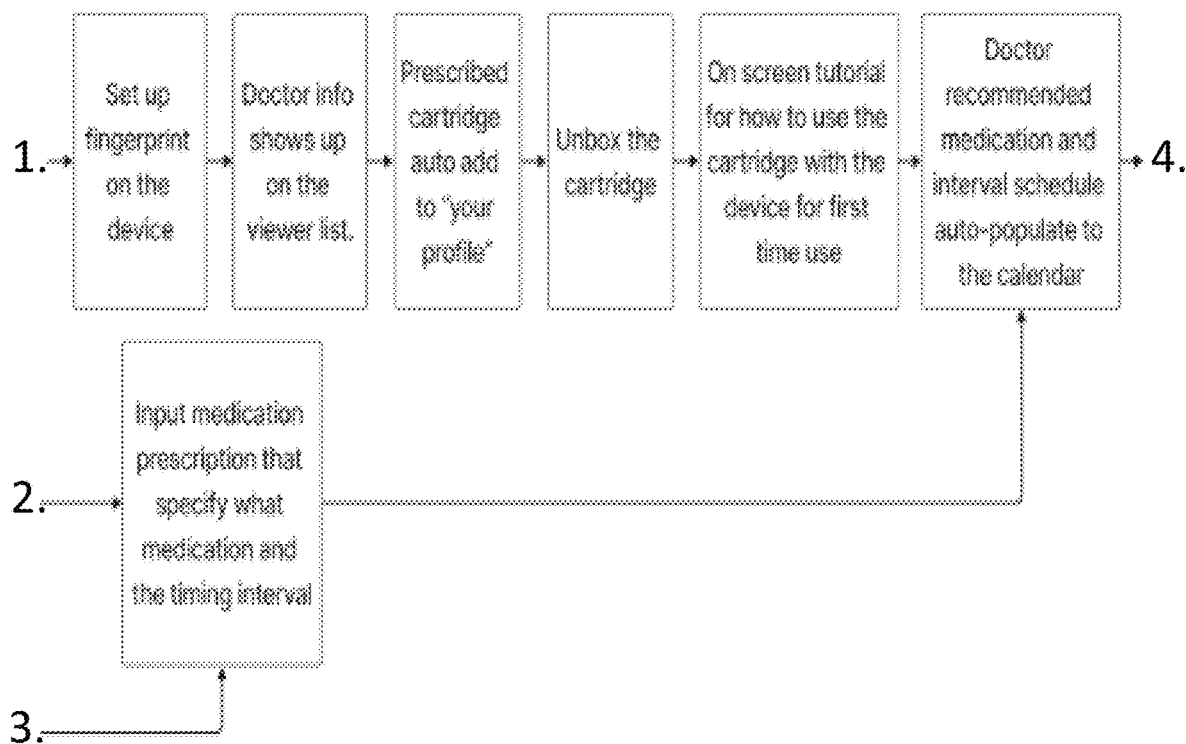
FIG. 18B is an illustration depicting the process flow of the patient scenario flowing from FIG. 18A.
Figure 18C:
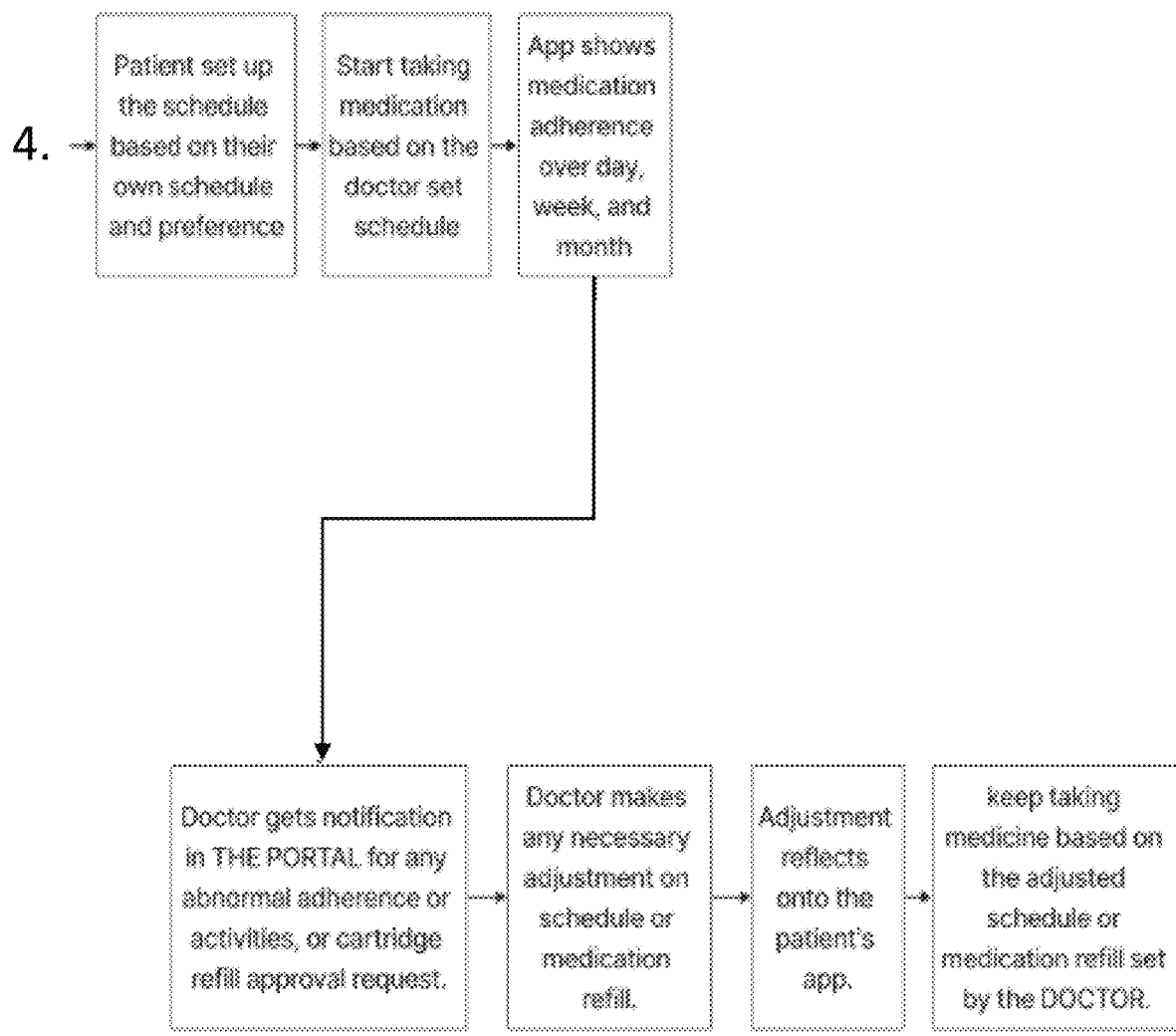
FIG. 18C is an illustration depicting the process flow of the patient scenario flowing from FIG. 18B.

FIGS. 18A through 18C depict an example patient scenario in which a regular patient needs to stay consistent on the medication as prescribed by his/her personal doctor. The patient receives a prescription for the medication dispending device and associated medication cartridge. The doctor then creates a profile in the doctor portal, generating an invitation link for the patient. The link can be transmitted to the patient to via text, email, or any other suitable transmission technique. Using this link, the patient creates an account for their patient system and associated medication dispensing device, where all prescription details and medication intervals are auto-populated for easy access and management. This setup allows the dispensing device to recognize the medication cartridge that is specifically prescribed for the patient, and the accompanying app (patient system) tracks usage and adherence. The link includes credentials that allow the physician system (i.e., doctor portal system) to interface with the patient system and/or caregiver system. The doctor can evaluate the data, make adjustments, or prescribe new refills as needed.

Figure 19A:
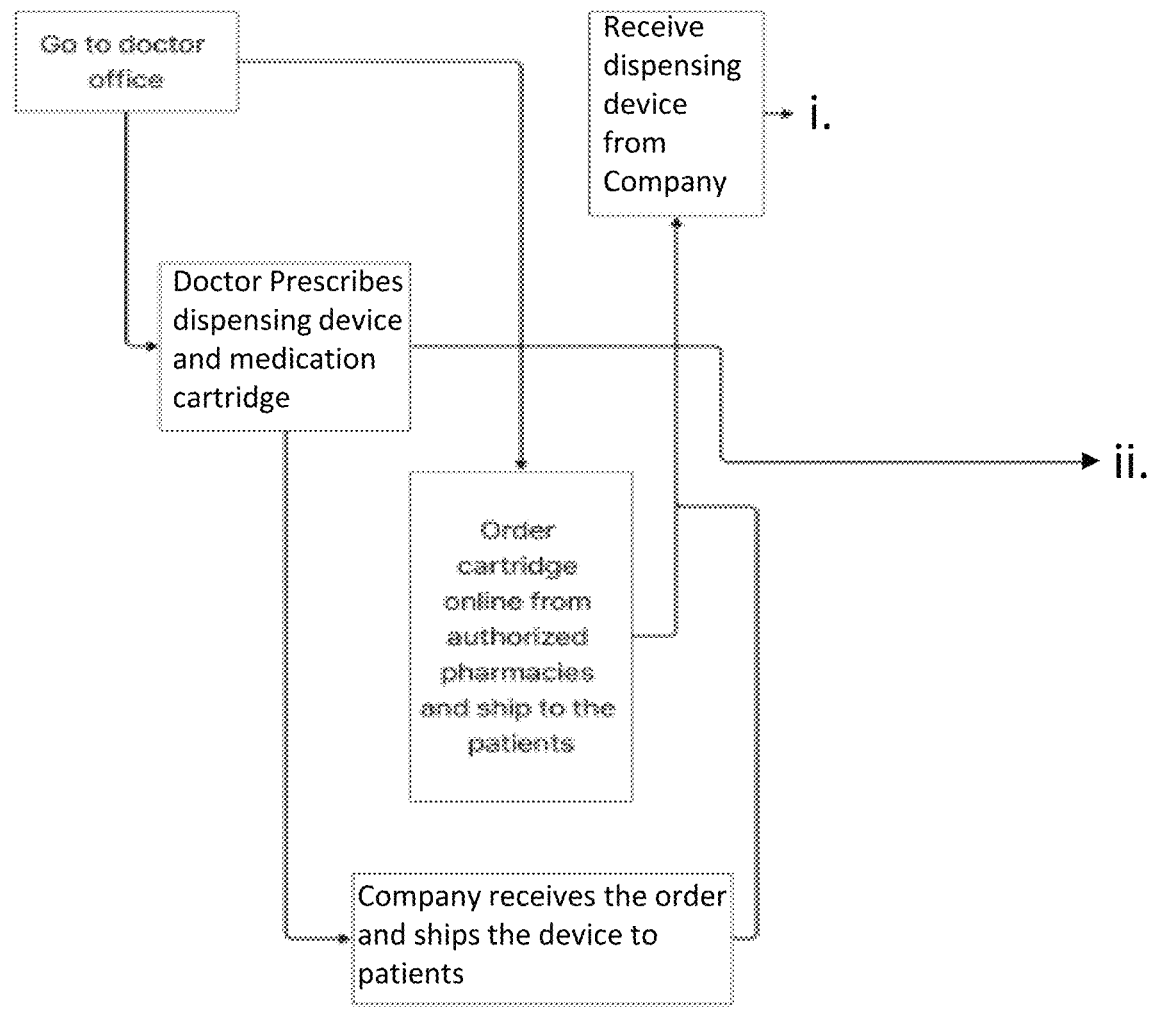
FIG. 19A is an illustration depicting a process flow for an example patient scenario and operation according to various embodiments of the present invention.
Figure 19B:
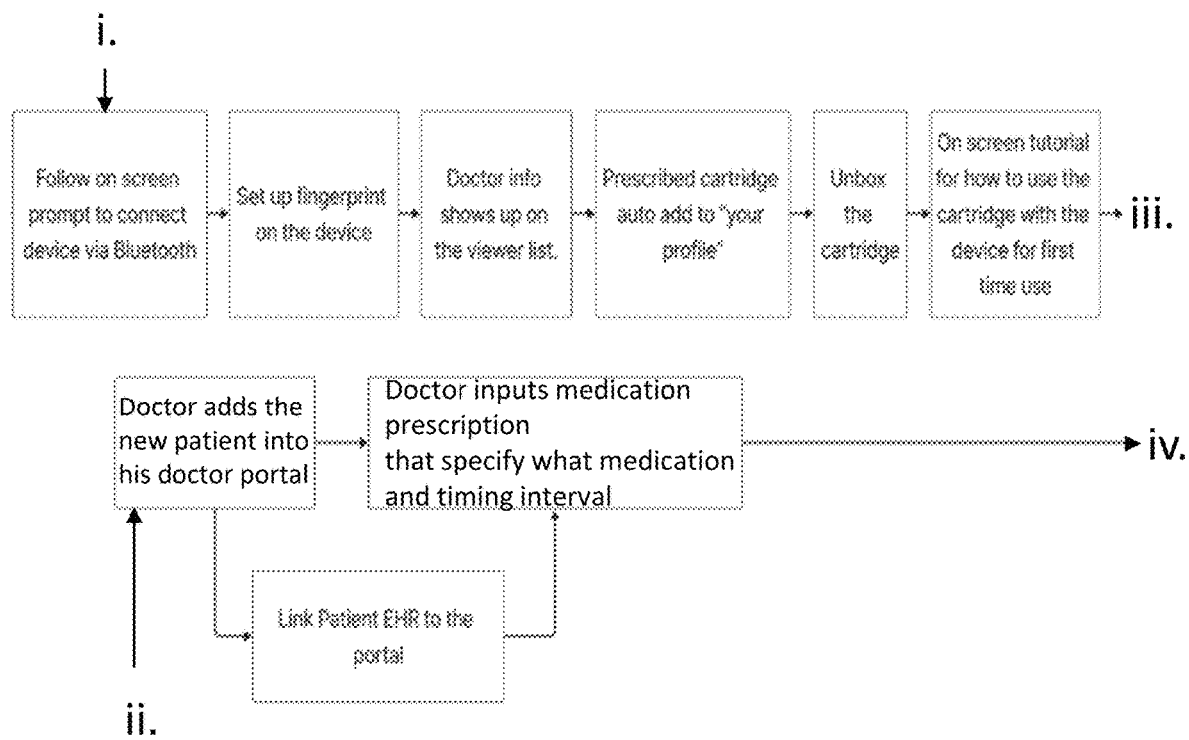
FIG. 19B is an illustration depicting the process flow of the patient scenario flowing from FIG. 19A.
Figure 19C:
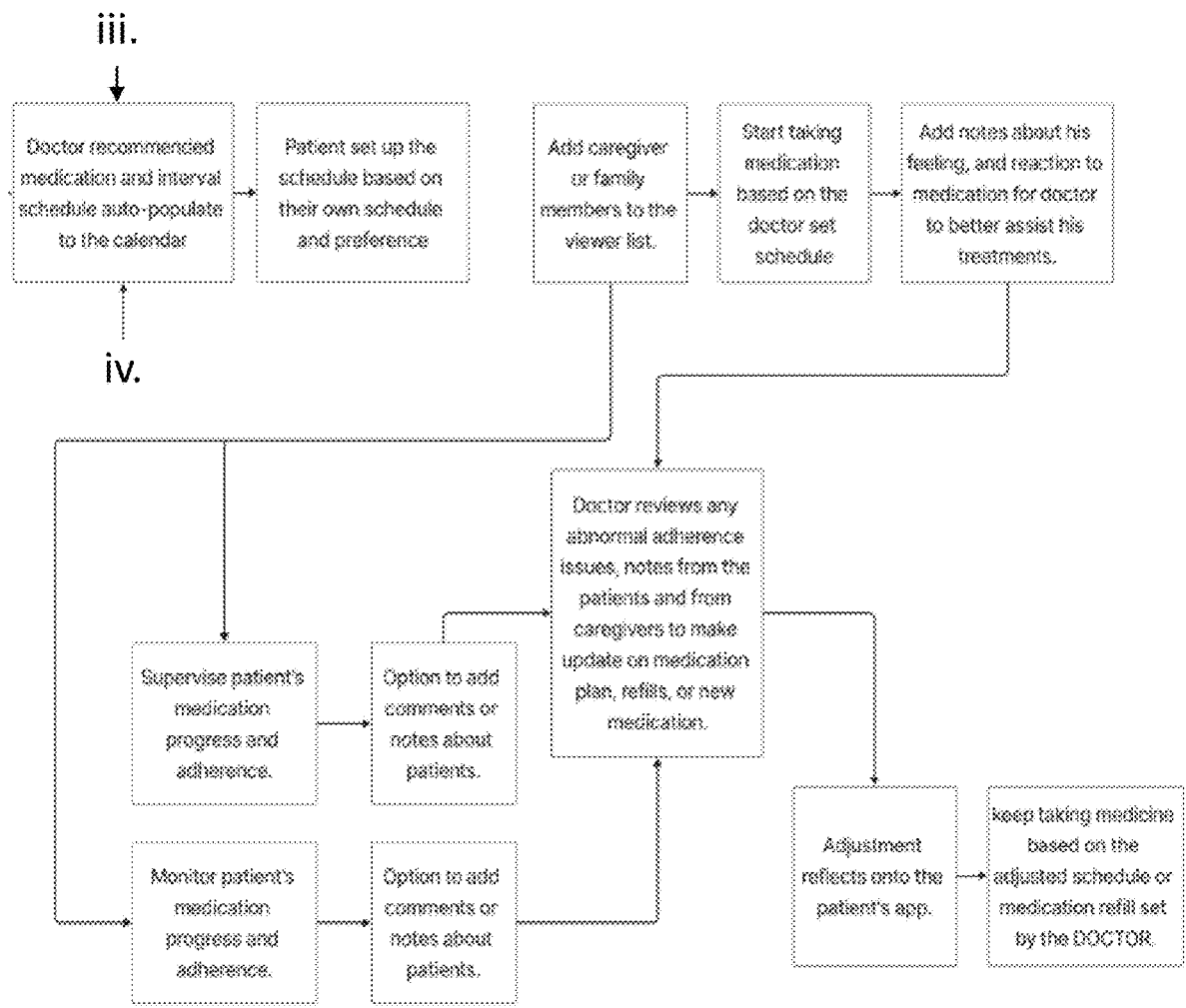
FIG. 19C is an illustration depicting the process flow of the patient scenario flowing from FIG. 19B.
Figure 20A:
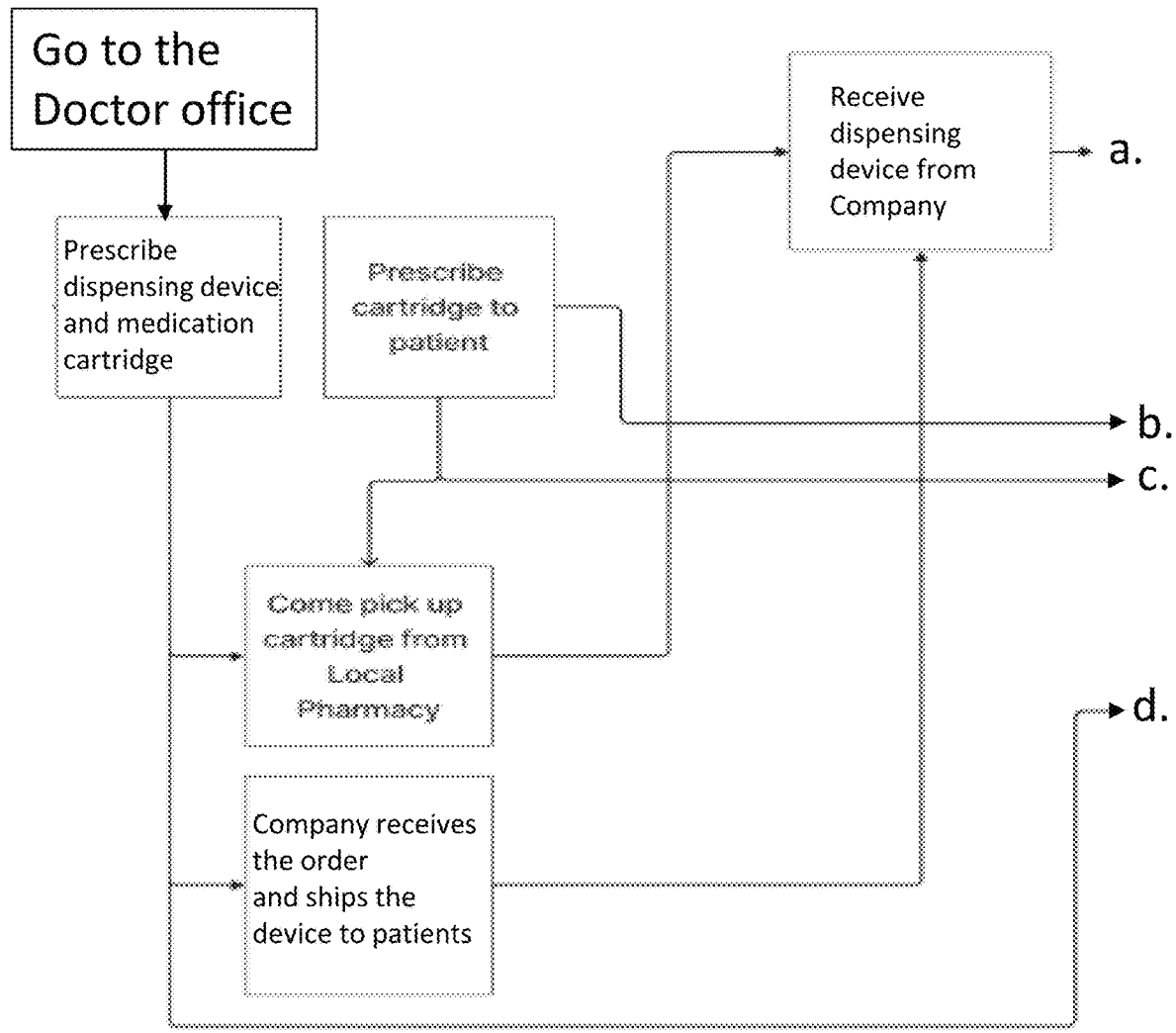
FIG. 20A is an illustration depicting a process flow for an example patient scenario and operation according to various embodiments of the present invention.
Figure 20B:
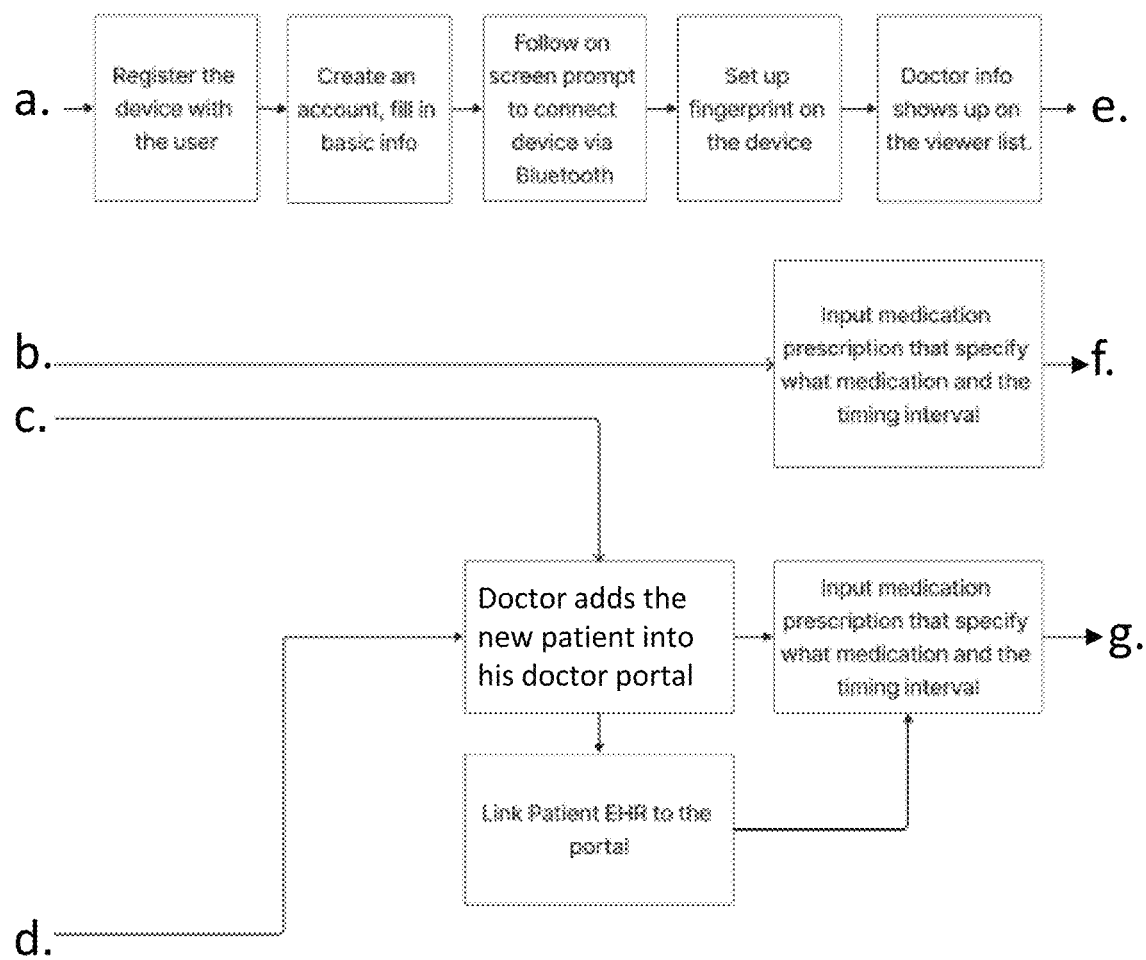
FIG. 20B is an illustration depicting the process flow of the patient scenario flowing from FIG. 20A.
Figure 20C:
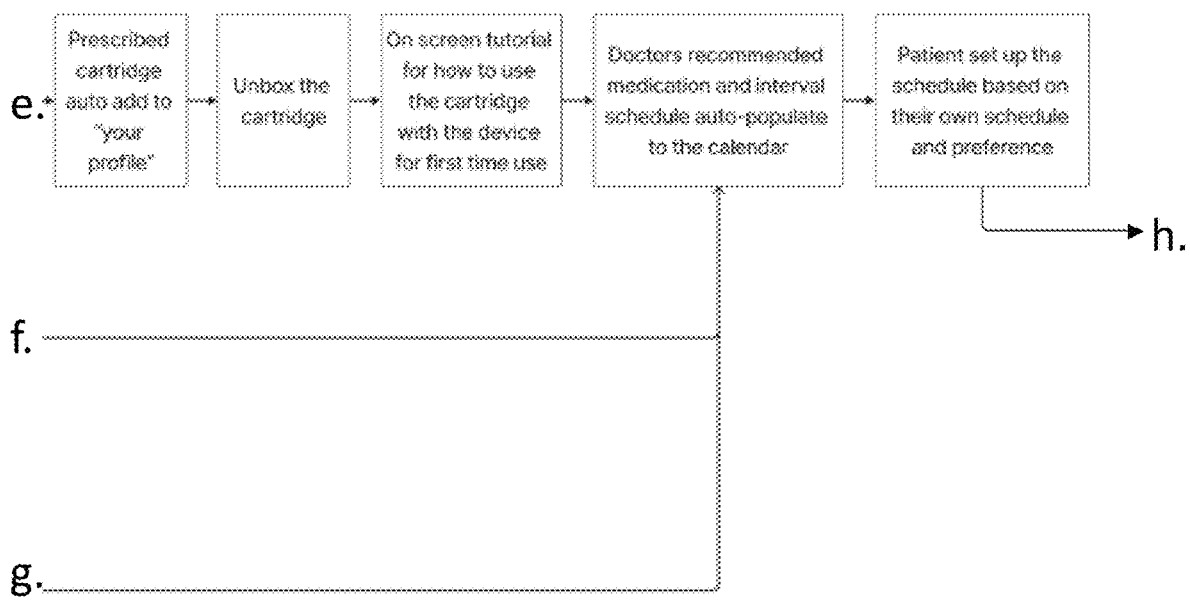
FIG. 20C is an illustration depicting the process flow of the patient scenario flowing from FIG. 20B.
Figure 20D:
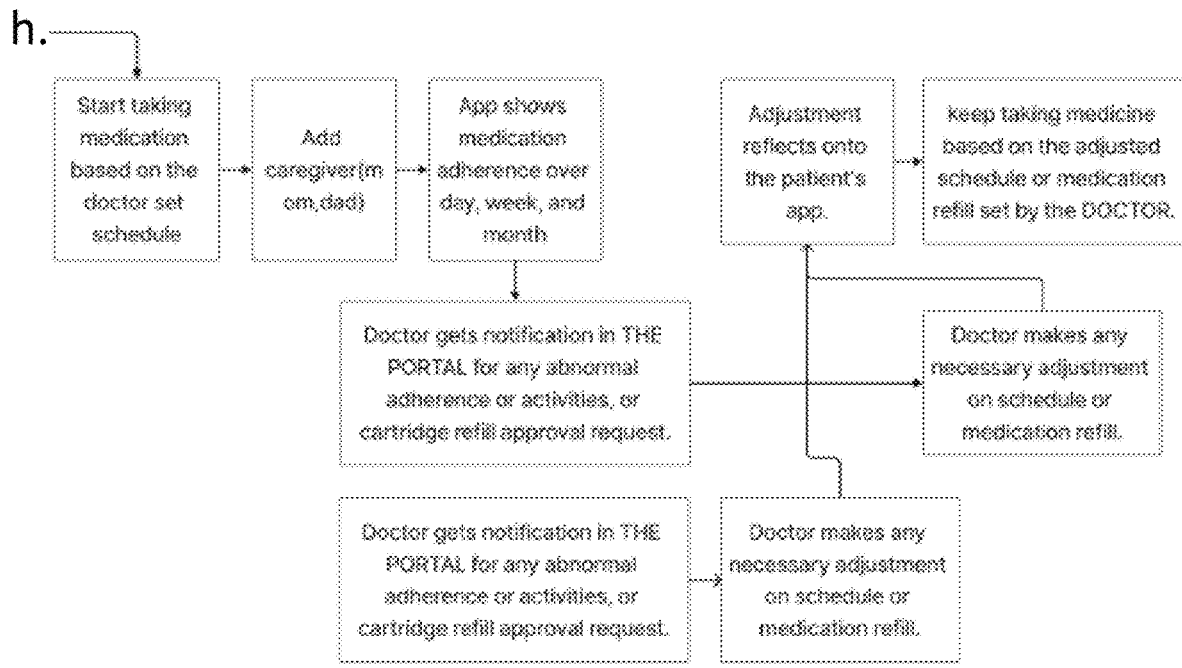
FIG. 20D is an illustration depicting the process flow of the patient scenario flowing from FIG. 20C.

Another example patient scenario is depicted in FIGS. 19A through 19C. For example, a variety of patients live in retirement communities where caregivers are responsible for supervising and taking care of multiple patients. The patient and caregiver systems allows the caregiver or family to supervise a patients treatment progress and add notes regarding how the patient responds to medication, etc. Such notes are helpful to the doctor to make accurate adjustments on the prescription and/or approve refills, etc. The notes, etc. are accessed by the doctor in the doctor portal system 1506 which allows the doctor to approve refills and adjust medication intervals on the doctor portal (e.g., housed on the remote server 1504 that is accessed by a doctor's personal computer, etc.) based on inputs from the caregiver and patient's relatives. As noted above, the doctor portal can be housed on the remote server or, in some aspects, be a modified caregiver system with doctor specific information.

For example and as shown in FIGS. 19A through 19C, the caregiver can log into the caregiver system at the beginning of their shift and view a list of all the senior patients under their care, along with their upcoming tasks and appointments displayed on the dashboard. The caregiver would review the medication reminders and administer medications to each senior patient accordingly. Throughout the day, the caregiver could use the communication tools in the caregiver system to coordinate with healthcare providers, update family members on their loved one's condition, and address any concerns that arise. At the end of their shift, the caregiver could document any observations or incidents in the system and review the activity logs to ensure all senior patients received proper care and attention.

Another example scenario is depicted in FIGS. 20A through 20D. For example, there are patients juggling multiple medications from different doctors and specialists. Such patients need to communicate with and get prescriptions from multiple doctors and specialists. The patient system, caregiver system, and doctor portal provides an all in one medication platform that allows such a patient to manage all of their medications while allowing doctors and specialists to easily stay informed with treatments and progress. The patient system, caregiver system, and/or doctor portal offers seamless management and tracking capabilities. Users can request prescription refills directly through the app as embodied in the patient system, eliminating the need for physical visits to their doctors. The app (as embodied in the patient system) also serves as a secure communication platform between patients and their healthcare providers, facilitating efficient interactions. Doctors can utilize medication adherence tracking tools within the app (via the patient system, caregiver system, and/or doctor portal system) to monitor patients' medication intake, ensuring adherence to prescribed regimens. This comprehensive solution proves invaluable for patients managing numerous medications and doctor visits simultaneously, streamlining their healthcare experience.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A caregiver system for interfacing with and controlling a medication dispensing device, the system comprising:
    one or more processors and associated memory, the memory being a non-transitory computer-readable medium having executable instructions encoded thereon, such that upon execution of the instructions, the one or more processors perform operations of:
    registering a caregiver;
    providing the caregiver a list of one or more patients under the caregiver's care and associated medication dose schedules for each of the one or more patients;
    modifying the dose schedule for at least one of the one or more patients to generate a modified dose schedule, each modified dose schedule having parameters specifying a particular medication and associated volume and timing interval for administration; and
    pushing the modified dose schedule to a patient system associated with a handheld medication dispensing device, the medication dispensing device having a housing with rotatable cartridge carrier and a medication cartridge therein, the medication cartridge containing the particular medication;
    wherein in pushing the modified dose schedule to the patient system, the patient system unlocks the medication dispensing device and causes the medication dispensing device to activate within the parameters of the modified dose schedule, such that in activating within the parameters of the modified dose schedule, an activator mechanism in the medication dispensing device rotates the cartridge carrier to move the medication cartridge within the cartridge carrier from a stored position to a dispensing position in which at least a portion of the medication cartridge is raised from the housing and at least partially exposed beyond the housing for actuation by the patient; and
    receiving notifications regarding patient adherence and providing an alert to a doctor when the patient fails to adhere to the dose schedule.

2. The caregiver system as set forth in claim 1, further comprising an operation of modifying authentication information regarding at least one of the one or more patients.

3. The caregiver system as set forth in claim 2, wherein modifying authentication information regarding at least one of the one or more patients includes editing a fingerprint record.

4. The caregiver system as set forth in claim 3, further comprising an operation of recording notes regarding at least one of the one or more patients for viewing by a user of an associated doctor portal system.

5. The caregiver system as set forth in claim 1, further comprising an operation of modifying authentication information regarding at least one of the one or more patients.

6. The caregiver system as set forth in claim 1, further comprising an operation of recording notes regarding at least one of the one or more patients for viewing by a user of an associated doctor portal system.

7. A computer program product for a caregiver to interface with and control a medication dispensing device, the computer program product comprising:
   a non-transitory computer-readable medium having executable instructions encoded thereon, such that upon execution of the instructions by one or more processors, the one or more processors perform operations of:
      registering a caregiver;
      providing the caregiver a list of one or more patients under the caregiver's care and associated medication dose schedules for each of the one or more patients;
      modifying the dose schedule for at least one of the one or more patients to generate a modified dose schedule, each modified dose schedule having parameters specifying a particular medication and associated volume and timing interval for administration; and
      pushing the modified dose schedule to a patient system associated with a handheld medication dispensing device, the medication dispensing device having a housing with rotatable cartridge carrier and a medication cartridge therein, the medication cartridge containing the particular medication;
      wherein in pushing the modified dose schedule to the patient system, the patient system unlocks the medication dispensing device and causes the medication dispensing device to activate within the parameters of the modified dose schedule, such that in activating within the parameters of the modified dose schedule, an activator mechanism in the medication dispensing device rotates the cartridge carrier to move the medication cartridge within the cartridge carrier from a stored position to a dispensing position in which at least a portion of the medication cartridge is raised from the housing and at least partially exposed beyond the housing for actuation by the patient; and
      receiving notifications regarding patient adherence and providing an alert to a doctor when the patient fails to adhere to the dose schedule.

8. The computer program product as set forth in claim 7, further comprising instructions for causing an operation of modifying authentication information regarding at least one of the one or more patients.

9. The computer program product as set forth in claim 8, wherein modifying authentication information regarding at least one of the one or more patients includes editing a fingerprint record.

10. The computer program product as set forth in claim 9, further comprising instructions for causing an operation of recording notes regarding at least one of the one or more patients for viewing by a user of an associated doctor portal system.

11. The computer program product as set forth in claim 7, further comprising instructions for causing an operation of modifying authentication information regarding at least one of the one or more patients.

12. The computer program product as set forth in claim 7, further comprising an operation of recording notes regarding at least one of the one or more patients for viewing by a user of an associated doctor portal system.

13. A computer-implemented method for a caregiver to interface with and control a medication dispensing device, the method comprising an act of:
   causing one or more processors to execute instructions encoded on a non-transitory computer-readable medium, such that upon execution, the one or more processors perform operations of:
      registering a caregiver;
      providing the caregiver a list of one or more patients under the caregiver's care and associated medication dose schedules for each of the one or more patients;
      modifying the dose schedule for at least one of the one or more patients to generate a modified dose schedule, each modified dose schedule having parameters specifying a particular medication and associated volume and timing interval for administration; and
      pushing the modified dose schedule to a patient system associated with a handheld medication dispensing device, the medication dispensing device having a housing with rotatable cartridge carrier and a medication cartridge therein, the medication cartridge containing the particular medication;
      wherein in pushing the modified dose schedule to the patient system, the patient system unlocks the medication dispensing device and causes the medication dispensing device to activate within the parameters of the modified dose schedule, such that in activating within the parameters of the modified dose schedule, an activator mechanism in the medication dispensing device rotates the cartridge carrier to move the medication cartridge within the cartridge carrier from a stored position to a dispensing position in which at least a portion of the medication cartridge is raised from the housing and at least partially exposed beyond the housing for actuation by the patient; and
      receiving notifications regarding patient adherence and providing an alert to a doctor when the patient fails to adhere to the dose schedule.

14. The computer implemented method as set forth in claim 13, further comprising an act of causing an operation of modifying authentication information regarding at least one of the one or more patients.

15. The computer implemented method as set forth in claim 14, wherein modifying authentication information regarding at least one of the one or more patients includes editing a fingerprint record.

16. The computer implemented method as set forth in claim 15, further comprising an act of causing an operation of recording notes regarding at least one of the one or more patients for viewing by a user of an associated doctor portal system.

17. The computer implemented method as set forth in claim 13, further comprising an act of recording notes regarding at least one of the one or more patients for viewing by a user of an associated doctor portal system.

* * * * *